(12) United States Patent
Johnson et al.

(10) Patent No.: US 10,426,590 B2
(45) Date of Patent: Oct. 1, 2019

(54) FILTERS WITH ECHOGENIC CHARACTERISTICS

(71) Applicant: VOLCANO CORPORATION, San Diego, CA (US)

(72) Inventors: Eric Johnson, San Diego, CA (US); Jeremy Stigall, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 303 days.

(21) Appl. No.: 14/773,440

(22) PCT Filed: Mar. 14, 2014

(86) PCT No.: PCT/US2014/027259
§ 371 (c)(1),
(2) Date: Sep. 8, 2015

(87) PCT Pub. No.: WO2014/152365
PCT Pub. Date: Sep. 25, 2014

(65) Prior Publication Data
US 2016/0015507 A1    Jan. 21, 2016

Related U.S. Application Data

(60) Provisional application No. 61/785,204, filed on Mar. 14, 2013.

(51) Int. Cl.
*A61F 2/01* (2006.01)
*A61B 8/08* (2006.01)
(Continued)

(52) U.S. Cl.
CPC .............. *A61F 2/01* (2013.01); *A61B 8/0833* (2013.01); *A61B 34/20* (2016.02); *A61B 90/39* (2016.02); *A61B 90/96* (2016.02); *A61F 2/013* (2013.01); *A61B 2090/3784* (2016.02); *A61B 2090/3925* (2016.02); *A61B 2090/3966* (2016.02);
(Continued)

(58) Field of Classification Search
CPC .... A61F 2/01; A61F 2/00; A61F 2/013; A61F 2002/011; A61F 2002/018; A61B 8/06; A61B 8/12; A61M 29/00
See application file for complete search history.

(56) References Cited

U.S. PATENT DOCUMENTS 152,652 A    6/1874  Knowlton
407,971 A    7/1889  Siersdorfer
(Continued)

FOREIGN PATENT DOCUMENTS

CN       2635045 Y      8/2004
CN     101965161 A      2/2011
(Continued)

OTHER PUBLICATIONS

Sihan et al., 2008, A novel approach to quantitative analysis of intraluminal optical coherence tomography imaging, Comput. Cardiol:1089-1092.
(Continued)

*Primary Examiner* — Vi X Nguyen

(57) ABSTRACT

There are described a variety of intravascular filters have wherein at least a portion of the filter has been modified to provide an enhanced echogenic characteristic of the filter.

15 Claims, 31 Drawing Sheets

(51) Int. Cl.
  *A61B 90/96* (2016.01)
  *A61B 34/20* (2016.01)
  *A61B 90/00* (2016.01)

(52) U.S. Cl.
  CPC . *A61B 2090/3995* (2016.02); *A61F 2002/011* (2013.01); *A61F 2002/016* (2013.01); *A61F 2002/018* (2013.01); *A61F 2250/0096* (2013.01)

(56) References Cited

U.S. PATENT DOCUMENTS

| | | |
|---|---|---|
| 621,937 A | 3/1899 | Niemann |
| 796,910 A | 8/1905 | Hernan |
| 1,950,378 A | 3/1934 | Andrews |
| 2,163,324 A | 6/1939 | Reinhold |
| 3,301,258 A | 1/1967 | Werner |
| 3,540,431 A | 11/1970 | Megin-Uddin |
| 3,617,880 A | 11/1971 | Cormack et al. |
| 3,789,841 A | 2/1974 | Antoshkiw |
| 3,841,308 A | 10/1974 | Tate |
| 3,952,747 A | 4/1976 | Kimmell |
| 4,140,364 A | 2/1979 | Yamashita et al. |
| 4,265,251 A | 5/1981 | Tickner |
| 4,274,423 A | 6/1981 | Mizuno et al. |
| 4,276,885 A | 7/1981 | Tickner et al. |
| 4,344,438 A | 8/1982 | Schultz |
| 4,398,791 A | 8/1983 | Dorsey |
| 4,401,124 A | 8/1983 | Guess et al. |
| 4,425,908 A | 1/1984 | Simon |
| 4,432,370 A | 2/1984 | Hughes et al. |
| 4,442,843 A | 4/1984 | Rasor et al. |
| 4,466,442 A | 8/1984 | Hilmann et al. |
| 4,494,531 A | 1/1985 | Gianturco |
| 4,552,554 A | 11/1985 | Gould et al. |
| 4,572,203 A | 2/1986 | Feinstein |
| 4,577,543 A | 3/1986 | Wilson |
| 4,619,246 A | 10/1986 | Molgaard-Nielsen et al. |
| 4,643,184 A | 2/1987 | Mobin-Uddin |
| 4,676,980 A | 6/1987 | Segal et al. |
| 4,682,895 A | 7/1987 | Costello |
| 4,718,433 A | 1/1988 | Feinstein |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,817,600 A | 4/1989 | Herms et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,832,055 A | 5/1989 | Palestrant |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,990,156 A | 2/1991 | Lefebvre |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,059,205 A | 10/1991 | El-Nounou et al. |
| 5,065,010 A | 11/1991 | Knute |
| 5,065,769 A | 11/1991 | de Toledo |
| 5,081,997 A | 1/1992 | Bosley et al. |
| 5,085,221 A | 2/1992 | Ingebrigtsen et al. |
| 5,095,911 A | 3/1992 | Pomeranz |
| 5,098,440 A | 3/1992 | Hillstead |
| 5,100,424 A | 3/1992 | Jang et al. |
| 5,120,308 A | 6/1992 | Hess |
| 5,125,137 A | 6/1992 | Corl et al. |
| 5,133,733 A | 7/1992 | Rasmussen et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,314 A | 4/1993 | Bosley et al. |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,234,458 A | 8/1993 | Metais |
| 5,240,003 A | 8/1993 | Lancee et al. |
| 5,240,437 A | 8/1993 | Christian |
| 5,242,460 A | 9/1993 | Klein et al. |
| 5,242,462 A | 9/1993 | El-Nounou et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,289,831 A | 3/1994 | Bosley |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,327,891 A | 7/1994 | Rammler |
| 5,336,178 A | 8/1994 | Kaplan et al. |
| 5,344,427 A | 9/1994 | Cottenceau et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,370,657 A | 12/1994 | Irie |
| 5,373,845 A | 12/1994 | Gardineer et al. |
| 5,373,849 A | 12/1994 | Maroney et al. |
| 5,375,602 A | 12/1994 | Lancee et al. |
| 5,375,612 A | 12/1994 | Cottenceau et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |

(56) References Cited

U.S. PATENT DOCUMENTS

| | | |
|---|---|---|
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,601,595 A | 2/1997 | Smith |
| 5,609,606 A | 3/1997 | O'Boyle |
| 5,626,605 A | 5/1997 | Irie et al. |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,725,550 A | 3/1998 | Nadal |
| 5,725,552 A | 3/1998 | Kotula et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,814,064 A | 9/1998 | Daniel et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,921,933 A | 7/1999 | Sarkis et al. |
| 5,925,055 A | 7/1999 | Adrian et al. |
| 5,925,060 A | 7/1999 | Forber |
| 5,944,738 A | 8/1999 | Amplatz et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,053,925 A | 4/2000 | Barnhart |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,080,178 A | 6/2000 | Meglin |
| 6,080,182 A | 6/2000 | Shaw et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,160,084 A | 12/2000 | Langer et al. |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,217,600 B1 | 4/2001 | Dimatteo |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,026 B1 | 7/2001 | Ravenscroft et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,388,043 B1 | 5/2002 | Langer et al. |
| 6,396,976 B1 | 5/2002 | Little et al. |

(56) References Cited

U.S. PATENT DOCUMENTS

| | | |
|---|---|---|
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,443,972 B1 | 9/2002 | Bosma et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,514,273 B1 | 2/2003 | Voss et al. |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,544,279 B1 | 4/2003 | Hopkins et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,620,183 B2 | 9/2003 | Dimatteo |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B2 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |

(56) References Cited

U.S. PATENT DOCUMENTS

| | | |
|---|---|---|
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,789,892 B2 | 9/2010 | Johnson et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,854,747 B2 | 12/2010 | Johnson et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,273,099 B2 | 9/2012 | Dimatteo |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |

(56) References Cited

U.S. PATENT DOCUMENTS

| | | |
|---|---|---|
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp, II et al. |
| 2002/0089335 A1 | 7/2002 | Williams |
| 2002/0095171 A1 | 7/2002 | Belef |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0193827 A1 | 12/2002 | McGuckin et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0171774 A1 | 9/2003 | Freudenthal et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186512 A1 | 9/2004 | Bruckheimer et al. |
| 2004/0186558 A1 | 9/2004 | Pavcnik et al. |
| 2004/0195512 A1 | 10/2004 | Crosetto |
| 2004/0199201 A1 | 10/2004 | Kellett et al. |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0177185 A1 | 8/2005 | Becker et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0020285 A1 | 1/2006 | Niermann |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0069405 A1* | 3/2006 | Schaeffer ............ A61F 2/01 606/200 |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0241675 A1 | 10/2006 | Johnson et al. |

(56) References Cited

U.S. PATENT DOCUMENTS

| | | |
|---|---|---|
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0033534 A1 | 2/2008 | Cook et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |

(56) References Cited

U.S. PATENT DOCUMENTS

| | | |
|---|---|---|
| 2010/0125648 A1 | 5/2010 | Zaharia et al. |
| 2010/0128348 A1 | 5/2010 | Taverner |
| 2010/0130963 A1 | 5/2010 | Ebert et al. |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0268265 A1 | 10/2010 | Krolik et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0034802 A1 | 2/2011 | Shrivastava |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0022638 A1 | 1/2012 | Leewood et al. |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0012981 A1 | 1/2013 | Johnson et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0023981 A1 | 1/2013 | Dierking et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0289519 A1 | 10/2013 | Johnson et al. |
| 2013/0289610 A1 | 10/2013 | Johnson et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |

(56) References Cited

U.S. PATENT DOCUMENTS

| | | |
|---|---|---|
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |
| 2015/0164630 A1 | 6/2015 | Johnson et al. |
| 2015/0173830 A1 | 6/2015 | Johnson et al. |
| 2015/0173884 A1 | 6/2015 | Johnson et al. |
| 2015/0173924 A1 | 6/2015 | Johnson et al. |
| 2016/0030151 A1 | 2/2016 | Johnson et al. |
| 2016/0030152 A1 | 2/2016 | Johnson et al. |

FOREIGN PATENT DOCUMENTS

| | | |
|---|---|---|
| EP | 1041373 A2 | 10/2000 |
| EP | 01172637 A1 | 1/2002 |
| EP | 2438877 A2 | 4/2012 |
| GB | 1588072 A | 4/1981 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 5/2005 |
| WO | 2005/102211 A1 | 11/2005 |
| WO | 2005102211 A1 | 11/2005 |
| WO | 2006/029634 A2 | 3/2006 |
| WO | 2006/034233 A1 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2008127983 A1 | 10/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2014144362 A1 | 12/2010 |
| WO | 2011/06886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012003369 A3 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).

(56) References Cited

OTHER PUBLICATIONS

Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17)18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.
Zitova et al., 2003, Image registration methods: A survey. Image and Vision Computing, 21(11):977-1000.
Kinney TB, Update on inferior vena cava filters, JVIR 2003; 14:425-440.
DeWeese MS, A vena cava filter for prevention of pulmonary embolism, Arch of Surg 1963; 86:852-868, incorporate herein by reference.
International Search Report and Written Opinion dated Nov. 2, 2012, for International Patent Application No. PCT/US12/53168, filed Aug. 30, 2013 (8 pages).
International Search Report and Written Opinion dated Apr. 14, 2014, for International Patent Application No. PCT/US2013/076148, filed Dec. 18, 2013 (8 pages).
International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 Pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).

(56) References Cited

OTHER PUBLICATIONS

International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846, Published Oct. 10, 2001.
Machine translation of JP 2000-321034, Sep. 5, 2002.
Machine translation of JP 2000-329534, Published Oct. 5, 2002.
Machine translation of JP 2004-004080, Published Aug. 1, 2004.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87(suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.

(56) References Cited

OTHER PUBLICATIONS

Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A—peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vase Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.

(56) References Cited

OTHER PUBLICATIONS

Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).

\* cited by examiner

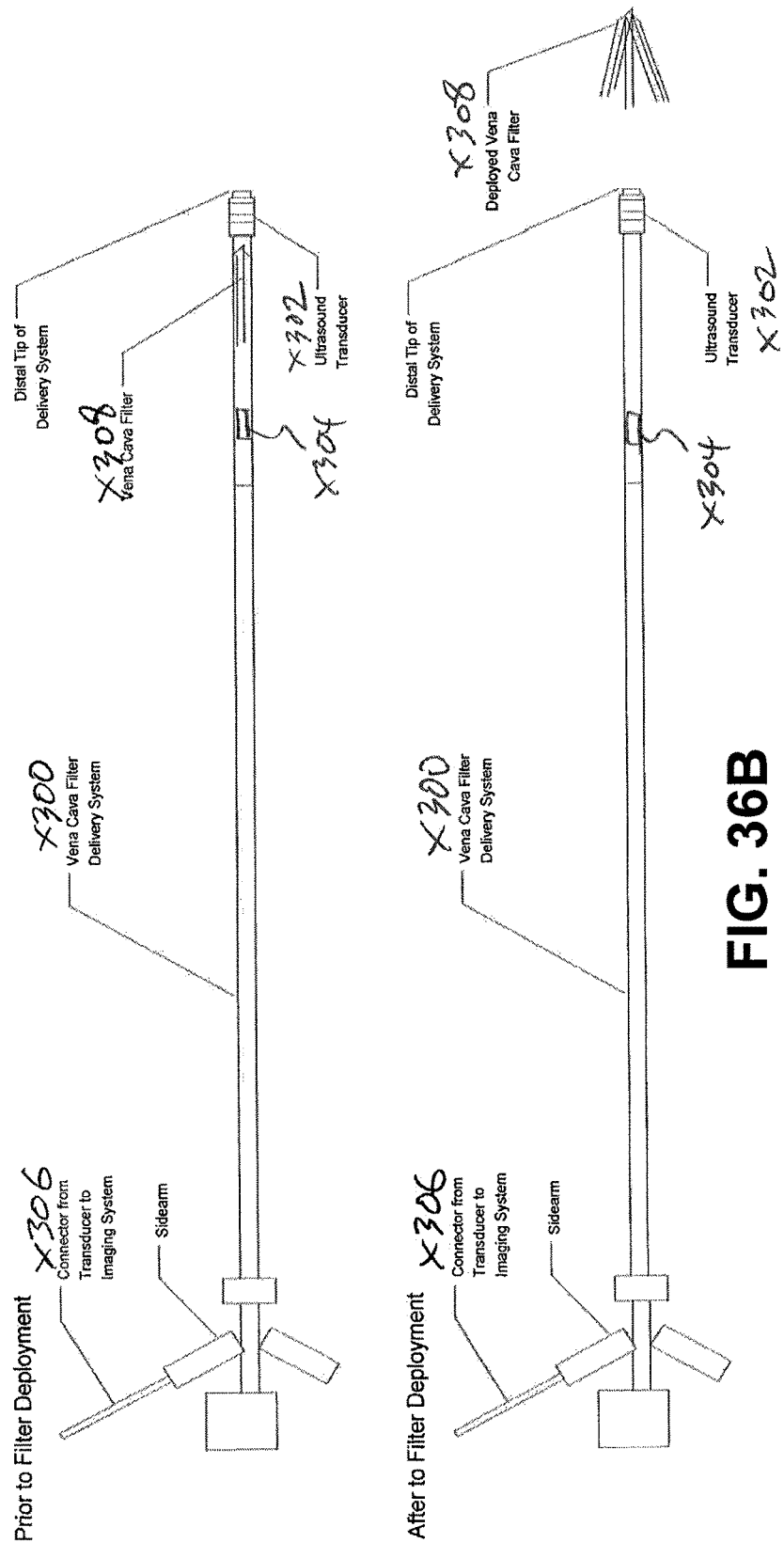

FILTERS WITH ECHOGENIC CHARACTERISTICS

CROSS REFERENCE TO RELATED APPLICATIONS

This application claims priority to U.S. Provisional Patent Application No. 61/785,204, filed Mar. 14, 2014, which is herein incorporated by reference in its entirety.

INCORPORATION BY REFERENCE

All publications and patents and patent applications mentioned in this specification are herein incorporated by reference to the same extent as if each individual publication or patent or patent application was specifically and individually indicated to be incorporated by reference.

FIELD

Aspects of the invention described herein relate generally to filters inserted into a patient's body and more particularly to the provision of echogenic coatings on such devices to enhance their visibility using one or more of in any combination ultrasound imaging, intravascular ultrasound imaging, greyscale intravascular ultrasound imaging, color intravascular ultrasound imaging or ultrasound image signal processing that included spectral analysis.

BACKGROUND

Ultrasonic imaging in the medical field is widely used for a variety of applications. In addition to imaging physiological structures and tissue such as organs, tumors, vessels, and the like, it is often desirable for a physician or technician to have an image of a medical device which has been inserted into the tissue or passageway of a patient. Still further, advancements in the use of intravascular or intraluminal imaging ultrasound (positioned either within or outside of the body) before, during and after procedures has led to increasing requirements for cooperation between device and imaging modality.

A variety of approaches have been used to enhance ultrasonic imaging of devices by increasing the acoustic reflection coefficient of the devices. While echogenic materials have been described for some uses in medical devices, the conventional uses of echogenic materials has not kept pace with the advancements in applications for imaging ultrasound. Moreover, while many approaches have been attempted, there is still need for improvements that are particular to the use of specific device designs. In particular, as medical therapies and procedures continue to advance, there is, in many medical instances, a need for more specific information about a device, its placement, position, orientation or aspect in relation to another object. What is needed are further improvements to the manner and placement of echogenic enhancements to obtain these additional benefits.

SUMMARY OF THE DISCLOSURE

In general, in one embodiment, a filter includes a hub; and a plurality of legs or wires or segments extending from the hub; wherein at least a portion of the hub or a portion of one or more of the legs or wires or segments is modified to provide an enhanced echogenic characteristic of the filter. This and other embodiments include one or more of the following features. In one aspect, the modification can provide an enhanced echogenic characteristic of the filter is a modification to a portion of the filter to enhance the echogenic characteristics of that portion of the filter. In another aspect, the modification can provide an enhanced echogenic characteristic of the filter which can be the formation of dimples into a surface of the filter. In yet another aspect, the dimples can be of sufficient number and scaled to a suitable size, shape, orientation and pattern for use with an intravascular ultrasound system. In a further aspect, the modification can provide an enhanced echogenic characteristic of the filter which can be the formation of protrusions formed in, placed on or joined to a filter surface. In an additional aspect, the protrusions can be of sufficient number and scaled to a suitable size, shape, orientation and pattern for use with an intravascular ultrasound system. In another aspect, the modification can provide an enhanced echogenic characteristic of the filter including the roughening one or more surfaces of a filter. In yet another aspect, the roughening can be performed using a chemical process, a laser or bead blasting technique. In still a further aspect, the roughening can be of sufficient scale to a suitable size, shape, orientation and pattern for use with intravascular ultrasound systems. In a further aspect, the modification can provide an enhanced echogenic characteristic of the filter including altering one or more steps of a filter manufacturing technique to introduce cavities, voids or pockets to locally modify or adapt one or more acoustic reflection characteristics to improve echogenicity in one or more specific regions of the filter. In an additional aspect, the cavities, voids or pockets can be of sufficient number and scaled to a suitable size, shape, orientation and pattern for use with an intravascular ultrasound system.

This and other embodiments include one or more of the following features. In one aspect, the filter can further include at least one fixation element. Any portion of the tissue anchor or any portion of one of the hub, the plurality of legs or wire or segments extending from the hub can be modified to provide an enhanced echogenic characteristic of the filter related to the use, status, position orientation of the at least one fixation element or the filter. In another aspect, the first and second support members, the crossover and the first end or the second end of the first support member, any portion of one of the above can be modified to provide an enhanced echogenic characteristic of the filter related to the use, status or of clot burden of the filter. In a further aspect, a method of positioning a filter within a lumen can include advancing a sheath containing a filter through the lumen, deploying a portion of the filter from the sheath into the lumen while maintaining a portion of the filter within the sheath, either of the above steps can be performed before or after using imaging from an intravascular ultrasound system. In an alternative aspect, a method of deploying a filter within a lumen can include advancing a sheath containing the filter through the lumen; and deploying the filter into the lumen, wherein, either step can be initiated, performed, confirmed or completed at least in part based on information obtained using intravascular ultrasound from one or more echogenic aspects of the filter. In yet another aspect, the method can further include maneuvering a snare towards the filter in a direction to retrieve the filter and engaging the snare with the filter. The maneuvering step or the engaging step can be initiated, performed, confirmed or completed at least in part based on information obtained using intravascular ultrasound from one or more echogenic aspects of the filter. In still another aspect, the method can further include engaging the lumen wall with a fixation element attached to the filter. This step can be initiated, performed, confirmed or completed at least in part based on information obtained using intravascular ultrasound from one or more echogenic aspects of the filter. In one aspect, a filter delivery catheter can be adapted and configured to deliver a filter according to any of the previously mentioned embodiments. A delivery catheter can be adapted and configured for delivery of an endoluminal filter, an IVUS transducer can be integrated into the distal portion of the delivery catheter, and one or more connectors on the proximal end of the delivery catheter can be adapted and configured to connect the IVUS transducer to an appropriate imaging or processing system. In another aspect, the filter delivery catheter can further include a telescoping sleeve within an moveable relative to the filter delivery catheter. In yet another aspect, the filter delivery catheter can further include a pusher rod within a moveable relative to the filter delivery catheter. In still another aspect, the IVUS transducer integrated into the distal portion of the delivery catheter can be adapted and configured whereby advancing and retracting the delivery catheter generates a plurality of images slices from the IVUS transducer. In a further aspect, the IVUS transducer integrated into the distal portion of the delivery catheter can be adapted and configured whereby advancing and retracting the delivery catheter can provide an output from the IVUS transducer for positioning guidance of a filter delivered using the delivery catheter. Is an alternative aspect, the IVUS transducer can be integrated into the distal tip or end of the delivery catheter. In yet another aspect, the delivery catheter can further include a pressure transducer. In still another aspect, the pressure transducer can be located proximal to the IVUS transducer. In one aspect, the delivery catheter can further include a filter as in any of the previously mentioned embodiments within the delivery catheter. In another aspect, a method of positioning a filter within a lumen can include advancing a delivery catheter according to any of the previously mentioned embodiments and can contain a filter as in any of the previously mentioned embodiments through the lumen using imaging information provided by the IVUS transducer on the delivery catheter to determine relative position before deploying a portion of the filter from the delivery catheter into the lumen to engage the lumen wall. In yet another aspect, the method can further include obtaining IVUS imaging of the lumen using the delivery catheter prior to deployment of the filter, after the deployment of the filter or during the deployment of the filter. In still another aspect, the method can further include obtaining IVUS imaging of the lumen using the delivery catheter for imaging a deployment location and estimating the sizing of a filter for the deployment location prior to performing any of the previously mentioned methods. In a further aspect, the method can further include estimating treatment duration using imaging data collected as in any of the previously mentioned methods. In an alternative aspect, a filter can further include an IVUS transducer integrated into the filter.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which:

FIGS. 36A and 36B, the pressure sensor and/or IVUS transducer are integrated into a delivery catheter, a retrieval catheter or a device itself.

DETAILED DESCRIPTION

Figure 1:
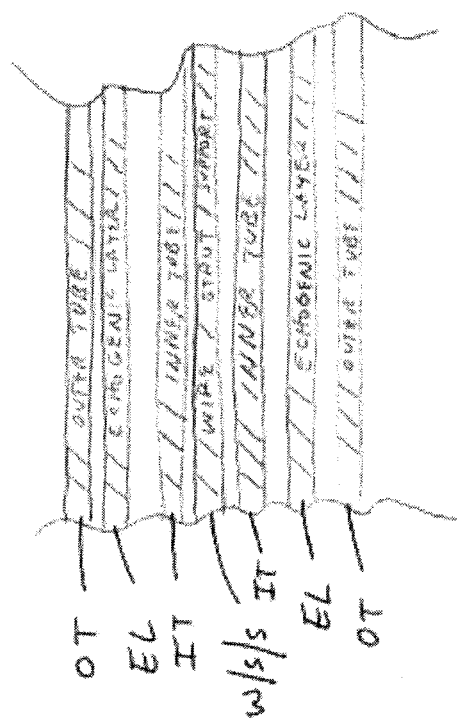
FIG. 1 is a section view of a wire strut or support element of a filter (w/s/s) having multiple segments in a concentric arrangement.

Filters are more complex structures in contrast to the relatively simple designs found in catheters and needles. In a more complex device like a filter there is a need to identify specific portions within the device during some medical procedures. In addition, it would be advantageous as well to determine the orientation of the device including components within the device to one another (as used for determining deployment, retrieval and the various intermediate stages thereof) as well as the overall filter orientation to the surrounding lumen or vessel. In contrast to the conventional techniques using location of the tip or start or end of the entire length, a more complex structure such as a filter position, orientation or relative placement information would yield specific benefits. In some cases, aspects, portions or attributes of the overall filter or filter components or portions will enable more useful determinations about the filter in relation to the physiological environment. In one aspect, an intravascular ultrasound (IVUS) catheter and processing system or signal processing algorithm is used to confirm filter sizing selection, guidance for filter placement, filter implantation steps, filter and/or vessel measuring using IVUS before during and/or after steps to confirm sizing selection and fit is appropriate under the physiologic environment and for confirmation and/or documentation of proper sizing selection, placement, engagement or degree of engagement of fixation elements (if present), clot burden, orientation and/or deployment in a patient or physician medical record.

In one aspect, embodiments of the present invention are directed toward medical devices having a complex shape or that are configured to move from stowed to deployed configurations that may also have specific orientation and placement criteria for proper use in a lumen, vessel or hollow organ. One such complex device is an IVC filter. Aspects of the present invention include such devices employed within the human body which have enhanced ultrasound visibility by virtue of incorporation of an echogenic material using any of the techniques described herein alone or in any combination.

In one aspect, there are described herein various alternative filter designs for increasing the echogenicity of the filter. A filter with enhanced echogenic characteristics may include one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. One example of the manufacturing alteration is to introduce gaps between the segments of tubing or coverings whereby the gap provides the echogenic enhancement. In addition, cavities, voids, pockets, dimples, gaps and the like may be left empty or, optionally, filed, partially filed or lined with any of the echogenic materials described herein.

In one aspect, there are provided embodiments of a filter having enhanced echogenic characteristics in or related to at least one or a portion of: an proximal end, a distal end, a terminal proximal end, a terminal distal end, a retrieval feature, an atraumatic tip on a retrieval feature, a mid-strut region, a leg or strut portion having at least one orientation attribute to another portion of the filter, an indicia of a location of a fixation element or a retrieval feature, a location on a portion of the filter selected such that in use with a particular fixation element the marker in in a location that indicates that the fixation element is fully deployed into a wall of a lumen or portion of a vessel or hollow organ (i.e., the marker is against the lumen wall or nearly so when the fixation element is fully engaged. As such, see the marker against the wall indicates proper deployment, spaced from or not visible would indicate, respectively, not fully engaged or over penetration); a portion of the distal tip and/or an elongated portion. The above described methods may also be applied to the other techniques and alternatives described herein.

In still further embodiments, a portion, component or aspect of an intraluminal filter may have enhanced echogenic attributes by applying a coating or sleeve containing one or more of the echogenic materials disclosed herein or fabricated according to any of the techniques or having any of the attributes to enhance echogenic qualities as described herein. In some aspects, the enhanced echogenic attributes are provided by the incorporation into, application onto or within a component or portion of a filter one or more echogenic materials or echogenic markers in a specific configuration, location, orientation or pattern on the filter.

Enhanced echogenic markers or locations may be devised and placed for use individually or in combinations such as to facilitate the identification to an IVUS system or ultrasound imaging modality an indication or signature for a specific location on a filter, such as, for example, a retrieval feature, a terminal proximal end, a terminal distal end, a location of a fixation element or a location of some other indicia that identifies a specific aspect of a particular filter design. In addition or alternatively, two or more enhanced echogenic markers or portions may be used in combination to provide additional information about a filter such as orientation with in a vessel, confirmation of deployment or a portion of a deployment sequence, confirmation of final placement, confirmation of migration or lack of migration, confirmation of retrieval or progress in a retrieval sequence and the like according to the various processes and used for filters within the vasculature or in lumens of the body. In another specific embodiment, the use of IVUS techniques with embodiment of the echogenic enhanced filters describe herein may also be used to measure the diameter of the vessel at specific device locations indicated by the echogenic markers during or after deployment or retrieval of a filter.

In still further aspects, the use of IVUS techniques with embodiment of the echogenic enhanced filters describe herein may also be used to determine, detect or indicate inadequate dilation, adequate dilation, filter expansion, degree of filter expansion, filter—vessel engagement and degree or engagement, strut/leg/anchor position and other attributes relating to the interaction between the filter and the surrounding physiological environment.

Still further, the echogenic markers are positioned with regard to the likely or planned positioning of the IVUS transducer and/or likely pathways for acoustic energy used by the imaging system. By way of example, if the IVUS transducer is forward looking, then those forward looking aspects of the filter will be provided with the enhanced echogenic aspects. In another example, if the IVUS transducer is cylindrically shaped and will be positioned through the interior portion of a filter then the filter will be provided with enhanced echogenic aspects on interior surfaces or portions that would receive acoustic energy from such as transducer in such a position. Other modifications are within the scope of the invention based on the particular style of IVUS transducer used, the position relative to the filter and the placement and type of echogenic feature incorporated into the filter. Put another way, the echogenic enhancements of the filters described herein are selected, designed and positioned on the filter with regard to the IVUS sensor type, acquisition mode and position relative to the filter. Additional details in the use of IVUS with filters is further described in U.S. Pat. Nos. 6,645,152 and 6,440,077, both of which are incorporated herein by reference in their entirety for all purposes.

In one aspect, the placement and signature of such enhanced echogenic markers are discernible to a human user viewing an ultrasound output alone or in combination with being discernible to a computer system configured for the processing of an ultrasound return including a return from the enhanced echogenic filter.

In various alternatives, the echogenic material may either be applied to a portion of or a component of a filter in any of a number of different techniques.

In one example, an echogenic component or additive is applied to or incorporated into a filter or portion of a filter as a selective coating applied to a portion or component of a filter.

In one example, an echogenic component or additive is applied to or incorporated into a filter or portion of a filter as a mold formed to be placed over or joined to a portion of component of a filter.

In one example, an echogenic component or additive is applied to or incorporated into a filter or portion of a filter as an extruded sleeve formed in a continuous segment to cover a portion or component of a filter. In one embodiment, one of the inner tubular member or the outer sleeve or coating may be fabricated of a material according to the present invention, having increased echogenicity, with the other of the inner tubular member fabricated of a biocompatible polymer such as polyurethane or silicone rubber, for example.

In one example, an echogenic component or additive is applied to or incorporated into a filter or portion of a filter as a compound or two layer structure comprising an inner tube and an outer tube or sleeve with one or both of the tubes made from or including or incorporating one or more echogenic materials or modifications as described herein. In addition or alternatively one or both sleeves, tubes described herein may include or encapsulate an echogenic marker or component of specific shape or geometry, for example, as in the case of a tube structure having within the sidewall of the tubing a coiled structure. In one aspect, the coiled structure is made from an echogenic material and the windings are provided in a manner that is useful in any of the aspects of the filter described herein. The coil may have a particular size or variation in size, pitch or variation in pitch or other attribute useful in providing an echo identifiable aspect of the filter property being determined. In one specific embodiment, the dimensions of the coil or other echogenic material has dimensions selected for increasing acoustic reflection with regard to the resolution or processing algorithms used in the imaging ultrasound system.

In one example, an echogenic component or additive is applied to or incorporated into a filter or portion of a filter as a braided structure incorporated into a compound or two layer structure comprising an inner tube and an outer tube or sleeve with one or both of the tubes made from or including or incorporating one or more braid comprising echogenic materials or modifications as described herein. In addition or alternatively one or both sleeves, tubes described herein may include or encapsulate an braid formed into an echogenic marker or component of specific shape or geometry, for example, as in the case of a tube structure having within the sidewall of the tubing a braided structure. In one aspect, the braided structure is made from an echogenic material and the braided is a small diameter that is when wound around the tubes or sleeve or directly onto a portion of or component of a filter. The winding pattern and spacing of the braided materials are provided in a manner that is useful in any of the aspects of the filter described herein. The braid may have a particular braid strand composition, structure, size or variation in size, pitch or variation in pitch or other attribute useful in providing an echo identifiable aspect of the filter property being determined. One or more of the strands in the braid may be formed from an echogenic material. One or more of the strands may be formed from a material having improved radiopaque characteristic. One or more of the strands may be formed from a material having both echogenic and radiopaque properties. The strands of a braid may be combined using any of the above described strand characteristics.

In another alternative, in still another example, an echogenic component or additive is applied to or incorporated into a filter or portion of a filter as the a series of short segments placed adjacent to one another along a portion or component of a filter in either a close packed or spaced arrangement. In another embodiment, the spacing or voids between adjacent segments may also be adjusted or selected so as to enhance echogenic capabilities of the filter using the material difference introduced by the spacings or voids.

In another alternative, in still another example, an echogenic component or additive is applied to or incorporated into a filter or portion of a filter as a tubing or sleeve suited to heat shrink operations. In one aspect, there is a manufacturing or assembly steps of sliding one or more sleeves over portion of the filter then apply heat to shrink down the segment about the portion of the filter. In particular, various embodiments provide for the specific placement of such a shrink fit tubing having enhanced echogenic characteristics as described herein. It is to be appreciated that the sleeves, segment or tubes may be provided from or have echogenic modifications or elements incorporated into suitable materials such as, for example, ePTFE, PTFe, PET, PVDF, PFA, FEP and other suitable polymers. Still further, these and other materials may be formed in shapes other than tubes but may also take the form of strands, lines, fibers and filaments to be applied in accordance with the echogenic enhancement techniques described herein. In some embodiments, the tubes or segments applied to a filter may have the same or different composition as well as have the same width or different widths. In one aspect, the width or thickness of a plurality of bands is used to provide a code or information about the filter. The use of echogenic bands of different widths is a marking technique similar to the way that different size and color rings on a resistor are arranged in a pattern to describe the resistor's value.

In another alternative, in still another example, an echogenic component or additive is applied to or incorporated into a filter or portion of a filter is extruded over a portion of or a component of the filter.

In another alternative, in still another example, an echogenic component or additive is applied to or incorporated into a filter or portion of a filter is by bonding an echogenic material or components to the filter using a suitable adhesive or bonding technique.

In any of the above described configurations, the portion or component of the filter may be modified with dimples, grooves, pockets, voids. In other aspects, there may be one or more full or partial circumferential recesses, rings, surface diffraction gratings or other surface features to selectively enhance or provide an echogenic property in that portion of the filter, to aid in or foster the application of the echogenic materials. In still further aspects, any of above described surface modifications may also be used to uniquely identify a portion of a filter or any of the above in any combination.

In still further aspects of any of the above echogenic markers or attributes the thickness of the sleeve or coating or component may decrease at its proximal and distal ends to provide for a smooth outer surface. As yet an additional alternative, a coating, marker or other echogenic material may extend proximally to or closely adjacent to the distal end or the distal end or both of the filter component or filtering device.

In still other alternatives or combinations, some filter design embodiments alter components of the filter to enhance echogenicity such as, for example, material selection to incorporate echogenic materials. Examples of echogenic materials include palladium, palladium-iridium or other alloys of echogenic materials.

In some embodiments, echogenic microbubbles are provided in a portion of a filter to enhance the acoustic reflections of that aspect of the filter. Echogenic microbubbles may be prepared by any convenient means and introduced into the component or portion thereof or by a coating or sleeve or shell or other transferring means or mixed with a polymer or other suitable base compound prior to extension of extrusion, molding casting or other technique. The echogenic microbubbles may be pre-prepared or prepared inside the component or element or marker as appropriate. Aspects of the preparation or use of microbubbles are described in U.S. Pat. Nos. 5,327,891; 4,265,251; 4,442,843; 4,466,442; 4,276,885; 4,572,203; 4,718,433 and 4,442,843. By way of example, echogenic microbubbles can be obtained by introducing a gas, e.g. carbon dioxide, into a viscous sugar solution at a temperature above the crystallization temperature of the sugar, followed by cooling and entrapment of the gas in the sugar crystals. Microbubbles can be formed in gelatin and introduced into a component or portion of a device. Microbubbles can also be produced by mixing a surfactant, viscous liquid and gas bubbles or gas forming compound, e.g. carbonic acid salt, under conditions where microbubbles are formed.

In still further alternatives, there is also the incorporation of dual mode materials (radiopaque and echogenic) into a polymer then used to form part of, be applied or otherwise incorporated with a filter device as described herein. Some of these polymer compounds may be fabricated to enhance aging and shelf life and have other beneficial attributes. In one aspect, a filter or portion thereof includes one or more selected segments that are constructed using visibility materials compounded with one or more polymeric materials that make the selected segments visible using both fluoroscopy and ultrasonic imaging. In one specific example, the visibility material may take the form of tungsten and/or tungsten carbide particles dispersed within a polymeric material. In one specific aspect, the radiopaque and echogenic material includes tungsten and/or tungsten carbide particles distributed within a base polymeric material.

In one embodiment, a portion of or a component of a filter includes or has been modified to have an inner layer including a radiopaque and echogenic material. In one alternative, the radiopaque and echo genic material includes particles distributed within a base polymeric material (i.e., a first polymeric material) including a polyether block amide; and an outer layer including an additional polymeric material (i.e., a second polymeric material). In certain embodiments, the additional polymeric material is a thermoplastic elastomer. Optionally, the additional polymeric material is more resistant to hydrolysis and/or oxidation than the base polymeric material.

In still further aspects, a component, a portion or an element added to a filter may be regarded as an echogenic body member that is a part of an echogenic filter to be sonically imaged. The echogenic body member is at least partially made up of a composite material which is echogenically imageable in the patient, such as by the use of ultrasonic imaging equipment used either within the patient or external to the patient. In one aspect, a composite material includes matrix material with discrete acoustic reflective particles embedded in matrix material. In one aspect, the matrix material is a biocompatible plastic. Examples of suitable plastics may include urethane, ethylene, silicone, polyethylene, tetrafluorethylene. In one aspect, a matrix is a formable, pliable material which may be molded and/or extruded to a variety of shapes, depending upon a specific application. The sound reflective particles are embedded in matrix material. Particles are, by way of example, made of a hard material, such as small glass particles that are solid or filled with an acoustically reflective medium. In one aspect, glass particles having a generally spherical shape forming glass microspheres. Glass microspheres with an outer diameter of about 5 microns is one acceptable size. Other sized particles may be utilized as, for example, ranging between 1 and 50 microns and beyond. Particles sized below the resolution size of the imaging ultrasound system in use may be arranged into patterns of sufficient size and orientation to the acoustic waves that result in a discernible feature by the imaging ultrasound system. Furthermore, the particles do not necessarily have to be spherical, or may be partially spherical. Still further, the shape of the particle could be altered to enhance acoustic reflection by presenting different shapes of particles, sizes of particles and combinations thereof to modify acoustic characteristics of the matrix material. By way of example, the particles may be shaped into an "Ordered array." "Ordered arrays" can take the form of a macrostructure from individual parts that may be patterned or unpatterned in the form of spheres, colloids, beads, ovals, squares, rectangles, fibers, wires, rods, shells, thin films, or planar surface. In contrast, a "disordered array" lacks substantial macrostructure.

By way of example, an echogenic marker may comprise particles that individually are below the resolution of the imaging ultrasound system. The echogenic marker is the combination of these below imaging ultrasound resolution particles in combination, in 1D, 2D or 3D patterns, in graphic arrays, or in machine readable combinations to make a signature. Based on the specific characteristics of the combination of particles, the acoustic returns from an echogenic marker or combination of echogenic markers may be visually perceptible in a display for interpretation by a user or may be detected and interpreted by one or more acoustic reflection or spectral processing algorithms within a imaging ultrasound processing system.

In one aspect, the echogenic material is fabricated by incorporating nanometer sized particles of sonically reflective materials, for example iron oxide, titanium oxide or zinc oxide into a biocompatible polymer. In one method of fabrication, the acoustically reflective particles are mixed with a powdered thermoplastic or thermosetting material such as a polyether amide, a polyurethane or an epoxy, or polyvinylchloride followed by thermal processing of the mixture to provide a material of increased sonic reflectance which may be applied as a coating on medical devices of the type discussed above or may be incorporated as a structural component of the medical devices as described herein.

In still further embodiments and aspects, the particles included to provide echogenic enhancements may be selected, arranged or incorporated to provide acoustically geometrically tuned nanostructures, microstructures or macrostructures. The particles provided herein are formable in all shapes currently known or to be created for acoustic reflection enhancement. In non-limiting examples, the nano-, micro- or macro-particles are shaped as spheres, ovals, cylinders, squares, rectangles, rods, stars, tubes, pyramids, stars, prisms, triangles, branches, plates or comprised of an acoustically reflective surface or where one or more surfaces is adapted such as by roughening or dimpling or other technique used to alter acoustic reflection properties. In non-limiting examples, the particles comprise shapes and properties such as plates, solid shells, hollow shells, rods, rice shaped, spheres, fibers, wires, pyramids, prisms, or a combination thereof.

In one specific aspect, a partially spherical surface may be provided on the outside and/or the inside of particles, as for example a particle with a hollow spherical space therein. Particles are made up of a different material than the matrix. While desiring not to be bound by theory, it is believed that a spherical shape provides for sound reflections at a variety of angles regardless of the direction from which the ultrasonic sound waves are emanating from, and accordingly, are more likely to reflect at least a portion of the transmitted signal back to the ultrasonic receiver to generate an image. Since many of matrix materials available are relatively ultrasonically transparent in a patient, sound reflective particles provide adequate reflection. The use of a composite, rather than a solution, provides adequate size for acoustic reflection off of the discrete particles embedded in the matrix. As indicated, a variety of materials may be utilized for the sound reflective particles, such as aluminum, hard plastic ceramics, and, metal and/or metal alloys particles, and the like. Additionally, liquids, gases, gels, microencapsulants, and/or suspensions in the matrix may alternatively be used either alone or in combination, so long as they form a composite with the desired ultrasonically reflective characteristic.

Any of the above embodiments, alternatives or filter modifications to enhance echogenic characteristics may also be designed or implemented in such a way as to provide an echogenic identifiable or unique trait or acoustic reflection signature that may be registered by a human operator looking at a display or identified using signal processing techniques of a return containing acoustic reflections from the filter in an imaging ultrasound system. In one example, there is a surface of the filter having one or more echo registerable or identifiable feature, mark or indication in a position useful for determining one or more of: a location of an end of a filter; a location of a fixation element on a filter; a location of a retrieval feature on a filter; an orientation of one or more of a leg, a strut, a filter or an end of a filter relative to another of a leg, a strut, a filter or an end or the orientation of the overall filter to a lumen, vessel or hollow organ in a body. Moreover, in another widely applicable aspect of providing enhanced imaging characteristics to a filter as described herein, the characteristic or modification—however added or incorporated into the filter—enable a filter, a filter component or a specified portion of a filter to be more readily imaged by intravascular ultrasound as described herein. In still another aspect, the characteristics or modification to the filter are oriented and positioned in order to facilitate IVUS imaging via an IVUS probe borne by a filter deployment or retrieval catheter, snare, or other implement provided to facilitate the use of intravascular filters.

FIG. 1 is a section view of a wire strut or support element of a filter (w/s/s) having multiple segments in a concentric arrangement. In this illustrative embodiment, the wire is encased in alternating tube segments. There is an inner tube (IT) directly adjacent to the wire. There is an echogenic segment layer (EL) adjacent to the inner layer. The inner tube may be selected to act as bonding layer to increase adhesion between the echogenic layer and the filter wire, strut or support member. In this embodiment, there is an outer tube (OT) over the echogenic layer. In alternative configurations, either or both of the inner tube or the outer tube may be omitted. The echogenic layer is a segment having one or more of the echogenic characteristics described herein.

FIGS. 2-7 provide various exemplary embodiments of a segment 87 having one or a plurality of one or more than one type of echogenic characteristic, property or feature added thereto. Each of the illustrated echogenic adaptations applied to segment 87 along with segment 87 itself may be sized, scaled and/or shaped as described herein as needed based upon the requirements of the portion of the filter and the echogenic characteristic.

Figure 2:
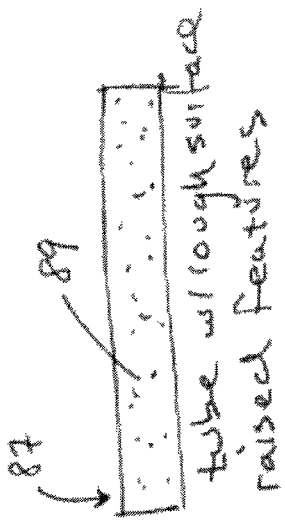
FIG. 2 is an embodiment of a segment having one or a plurality of laser drilled holes formed therein.

FIG. 2 is an embodiment of a segment 87 having one or a plurality of laser drilled holes 88 formed therein. The diameter and the shape of the holes may be selected based upon the size of the filter or filter component to which the segment 87 will be attached. The holes 88 may be completely through the wall of the segment or only partially through the wall. The holes 88 may be formed in any pattern, spacing or orientation as described herein.

Figure 3:
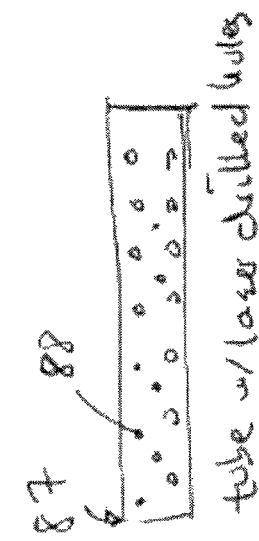
FIG. 3 is an embodiment of a segment having one or a plurality of raised features or alternatively roughed portions formed thereon.

FIG. 3 is an embodiment of a segment 87 having one or a plurality of raised features or alternatively roughed portions 89 formed thereon. The size and shape of the raised features or the roughness of the surface may be selected based upon the size of the filter or filter component to which the segment 87 will be attached. The raised features or portions of roughness 89 may be formed in any pattern, spacing or orientation as described herein.

Figure 4:
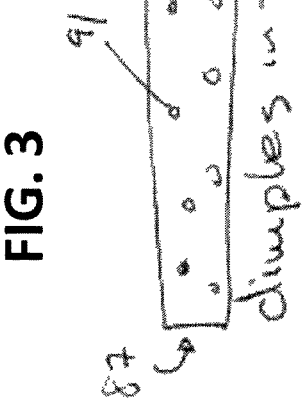
FIG. 4 is an embodiment of a segment having one or a plurality of bubbles formed therein.

FIG. 4 is an embodiment of a segment 87 having one or a plurality of bubbles 90 formed therein. The size, shape, pattern, and manner of incorporating one bubble 90 or a plurality of bubbles 90 into the segment 87 may be selected based upon the size of the filter or filter component to which the segment 87 will be attached. The bubbles 90 may be formed within the segment sidewall, near the surface of the segment sidewall or near the inner surface of the sidewall. The bubble or bubbles 90 may be formed in any pattern, spacing or orientation as described herein.

Figure 5:
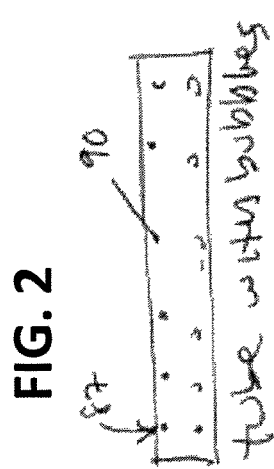
FIG. 5 is an embodiment of a segment having one or a plurality of dimples formed therein.

FIG. 5 is an embodiment of a segment 87 having one or a plurality of dimples 91 formed therein. The diameter and the shape of the dimples may be selected based upon the size of the filter or filter component to which the segment 87 will be attached. The dimples 91 may be formed in any pattern, spacing or orientation as described herein.

Figure 6:
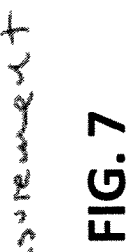
FIG. 6 is an embodiment of a segment having a coil or braided structure within or about the segment.

FIG. 6 is an embodiment of a segment 87 having a coil or braided structure 92 within or about the segment 87. The size, shape, pattern, and manner of incorporating the coil or braid 92 into the segment 87 may be selected based upon the size of the filter or filter component to which the segment 87 will be attached. The coil or braid 92 may be formed within the segment sidewall, near the surface of the segment sidewall or near the inner surface of the sidewall. The coil or braid 92 may be part of a sandwich structure as illustrated and described in FIG. 1. The coil or braid 92 may be formed in any pattern, spacing or orientation as described herein to enhance the echogenic characteristics of the filter or filter portion attached to the segment 87. The coil or braid 92 may be continuous along the entire length of a segment 87 or, alternatively, the coil or braid 92 may be in short lengths selected so that a plurality of coils or braids are provided within a single segment 87.

Figure 7:
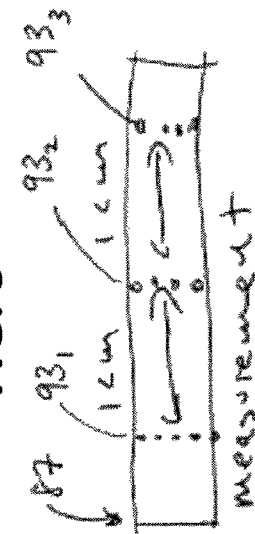
FIG. 7 is an embodiment of a segment having a plurality of echogenic markers arrayed in rings about the segment to provide an indication of measurement via the spacing between adjacent rings.

FIG. 7 is an embodiment of a segment 87 having a plurality of echogenic markers 93 arrayed in rings 93.1, 93.2 and 93.3. For purposes of illustration the rings are shown in an orientation that is generally orthogonal to the central longitudinal axis of the segment 87. The rings are shown with a sample spacing of 1 cm between them. The spacing may be any suitable distance based on the factors described herein such as filter size and physiological environment. Similarly, the rings may be angled in other orientations relative to the longitudinal axis of the segment. For example, some ring may be in one angular orientation while other rings may be in a different angular orientation where the angular orientation or patent of orientation is utilized to provide one or more of the filter functionality or echogenic characteristics described herein. In some specific configurations, the spacing and sizes used are in the millimeter range. In some specific configurations, the spacing and sizes are in the micron range. In some specific configurations, the size and/or spacing of a ring or between adjacent rings are in a combination of mm and micron ranges for sizes, spacings and features. The size and spacing of the echogenic markers 93 may be selected based upon the size of the filter or filter component to which the segment 87 will be attached. The markers 93 may be formed in any pattern, spacing or orientation as described herein in order to facilitate a measurement using the markers. Still further, the markers 93.1, 93.2 and 93.3 may be utilized for provide for other filter characteristics as described herein.

Figure 8:
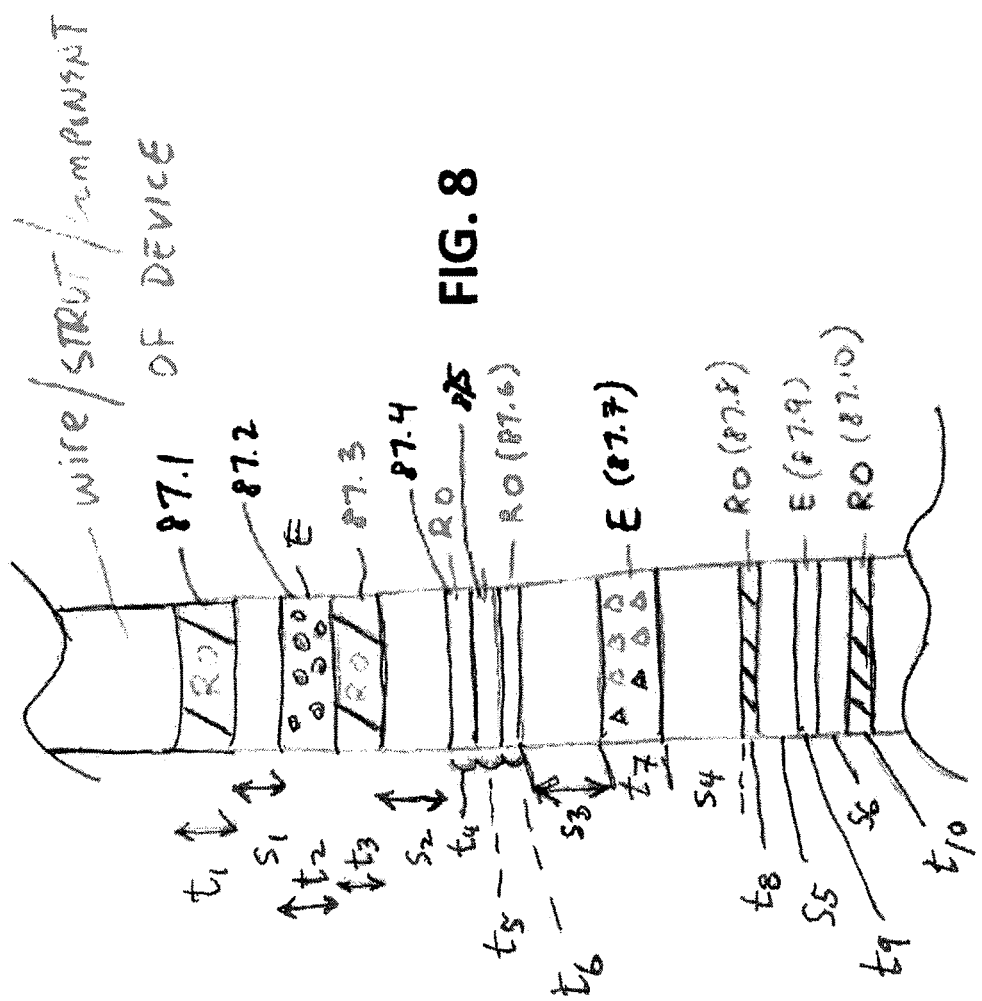
FIG. 8 illustrates various alternative configurations for a segment used alone or in conjunction with other segments.

FIG. 8 illustrates various alternative configurations for a segment used alone or in conjunction with other segments. The segments are illustrated along an exemplary wire, strut, or component of a filtering device. The segments may have different characteristics to enable the segment to be more readily imaged by a medical imaging modality used externally, internally or intraluminally. In one aspect, the segment characteristics are selected to provide for imaging enhancements for a filter being used within a vein or an artery. In another aspect, the segments may have different characteristics to enable the segment to be readily imaged by intravascular ultrasound as described herein. In still another aspect, the segments are oriented and positioned in order to facilitate IVUS imaging via an IVUS probe borne by a filter deployment or retrieval catheter, snare, or other implement. In one illustrative embodiment, the segments are selected and arrayed to facilitate imaging utilizing IVUS and an external medical imaging modality. In one exemplary embodiment, the external imaging modality is x-ray.

Also illustrated in FIG. 8 is the use of a combination of different echogenic characteristics (designated E) and radio-opaque characteristics (designated RO). These characteristics may be any of those described herein in any combination. The echogenic characteristic of a segment may be the same as another segment in a grouping such as in the E segments 87.9 and 87.5. Alternatively, the echogenic characteristic of a segment may be different from those in an adjacent group as with segments 87.2, 87.5 and 87.7.

FIG. 8 also illustrates not only that different characteristic and properties of segments may be used but also how variable segment dimensions may be used to aid in echogenic enhancement of a filter. As illustrated, the segments have different widths or thicknesses as indicated along the longitudinal axis of the wire, strut or component. As such, FIG. 8 illustrates a series of imagine enhancing segments 87.1-87.10 having a variety of width or thickness values t1-t10. In one embodiment, the segments are configured as short rings or bands. The thickness of segments in groups may be similar as illustrated in segments 87.1, 87.2 and 87.3 where the thicknesses t1, t2 and t3 are about the same. Similarly, segments 87.4, 87.5 and 87.6 illustrate segments of similar width or thickness where t4, t5 and t6 are about the same value. Similarly, segments 87.8, 87.9 and 87.10 illustrate segments of similar width or thickness where t8, t9 and t10 are about the same value.

FIG. 8 also illustrates how segments within a group or groups of segments may have a variety of different spacing (s1-s6) to provide enhancements to a filter for improving medical imaging modality characteristics. For example, in the segment grouping of 87.1, 87.2 and 87.3, there is a spacing s1 between segment 87.1 and segment 87.2 but then no spacing between segments 87.2 and 87.3. A spacing s2 is shown between segment 87.3 but then no spacing in the combination segment grouping formed by segments 87.4, 87.5 and 87.6. A spacing of s3 is shown between the three segment combination of 87.4, 87.5 and 87.6 to the single segment 87.7. The single segment 87.7 is spaced apart by spacing s4 from the equally sized (i.e., t8=t9=t10) and equally spaced (i.e., s5=s6) group of segments 87.8, 87.9 and 87.10. It is to be appreciated that in various alternative embodiments, the spacing used in groups of segments or between groups of segments may be the same or variable.

Figure 9:
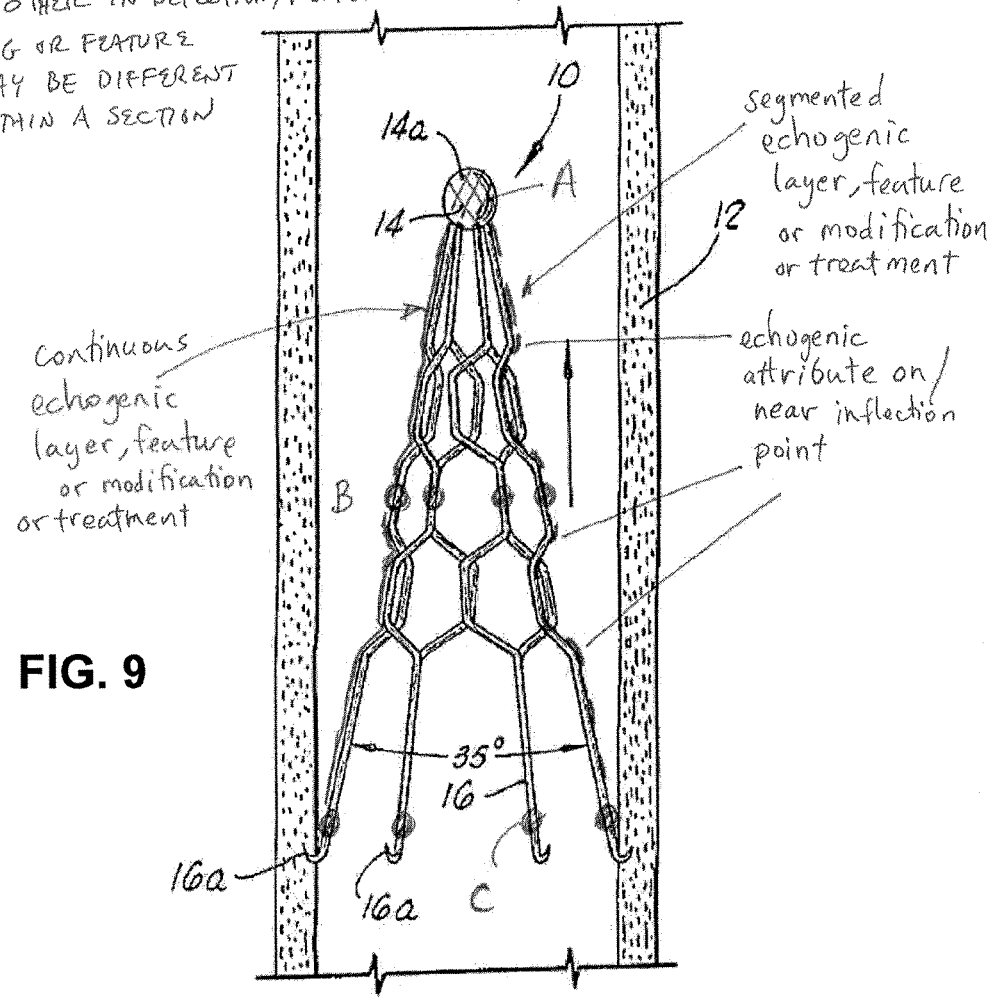
FIG. 9 is a view of an exemplary filter illustrating various alternative aspects of providing a filter with improved echogenic characteristics.

FIG. 9 is a view of an exemplary filter illustrating various alternative aspects of providing a filter with improved echogenic characteristics. The filter illustrated is a conical filter. It is to be appreciated that the filter of FIG. 9 is merely representative of one type of filter. It is to be appreciated that the various alternative enhancement, modifications and treatments described herein may be provided to any intravascular or intraluminal filter. The exemplary filter is dividing into three general sections A. B and C. Sections A, B and C may be the same type of enhancement or have an enhancement different from one another section. In addition, the type of enhancement in each section may be the same or different from one another in detection, response or appearance under ultrasound. In addition, a tag, feature or enhancement may be different within a section. Circles 902 are used to indicate exemplary locations for an echogenic feature, tag, marker or modification to an enhanced filter 10. The illustrative embodiment in FIG. 9 also illustrates a continuous echogenic layer, feature or modification or treatment 908. The illustrative embodiment in FIG. 9 also illustrates an echogenic attribute on/near an inflection point 906 in an enhanced filter structure 10. The illustrative embodiment in FIG. 9 also illustrates a segmented echogenic layer, feature or modification or treatment 904 on an enhanced filter structure 10. Section A is considered the apex, tip, distal portion or terminal end depending upon filter configuration. Section B is considered the mid-strut, middle, filtration portion, debris capture portion, or thrombus collection or lysing portion depending upon specific filter configuration. Section C is considered the rear portion, proximal portion, proximal terminal portion, anchor, fixation or perforation portion depending upon a specific filter configuration. It is to be appreciated as well that the echogenic features, tags, markers or modifications illustrated for sections A, B and/or C may be of the same type or different types depending upon the echogenic signature or attribute intended for that section, group or sections or filter. As such, the echogenic features, tags, markers or modifications for a particular section may be selected from any of the various alternatives described herein.

Echogenic characteristics may be added to each of the sections based on the type of function being measured or characterized. For example, echogenic markers, features or tags may be added to Section A in order to provide, for example: identification of the terminal end, end portion or retrieval portion of a filter. Echogenic characteristics of Section A may also be used for determinations related to Section A specifically or the filter generally of filter position, positioning, attitude within the lumen, localization of the filter within the vasculature and other traits common to the characterization of intravascular devices. For example, echogenic markers, features or tags may be added to Section B in order to provide, for example: identification of the mid strut portion, middle or capture region. Echogenic characteristics of Section B may also be used for determinations related to Section B such as for sizing, centering, symmetry of implantation, placement, apposition of implant to vessel walls, clot burden, deployment status or completion, gauge of filter capacity and/or filter contents as well as filter position, positioning, attitude within the lumen, localization of the filter within the vasculature and other traits common to the characterization of intravascular devices. For example, echogenic markers, features or tags may be added to Section C in order to provide, for example: identification of the rear portion, terminal end, retrieval feature, anchor location or depth of insertion, perforation indication or other aspects of the rear or proximal portion of a filter. Echogenic characteristics of Section C may also be used for determinations related to Section C such as for sizing, centering, symmetry of implantation or placement of legs struts and the like, as well as for determination of wall apposition, anchor penetration or perforation. Still further, the markers or tags may be added to aid in determining or evaluating filter position, positioning, attitude within the lumen, localization of the filter within the vasculature and other traits common to the characterization of intravascular devices.

A filter having enhanced echogenic properties is illustrated in FIG. 9 as it appears when it is in operative position within the vasculature. In one specific aspect the filter is in use in a large blood vessel. One exemplary vessel is the vena cava. Still further, a modified filter may be employed in a different vein or even an artery. The filter is designated generally by reference numeral 10, and the wall of the blood vessel in which it is located is designated by reference numeral 12. The filter 10 includes an apical hub 14 of overall egg-shaped or tear drop configuration and which has a generally hemispherically shaped end portion 14*a*.

The filter 10 includes a plurality of elongated legs 16 which are of equal length and are identically configured to each other. The legs 16 are collectively arrayed in a conical geometric configuration so that the legs converge to the apical hub 14, and are symmetrically spaced about a central axis extending through the hub. Each of the legs is of equal diameter over its entire length and is made of a relatively resilient material, such as tempered stainless steel wire or the like. In addition to the echogenic attributes described herein, the legs may be coated with a polymeric, synthetic resin material having anti-thrombogenic properties. FIG. 9 illustrates an echogenic marker at the tip 14. Exemplary continuous echogenic layers, features or modifications are also illustrated along one or more legs of the filter. In addition, FIG. 9 illustrates the use of echogenic tags, features or markers at, along or near inflection points in a filter element or component. In addition, FIG. 9 illustrates to application of echogenic markers, tags or features near the fixation elements of the filter.

Figure 10:
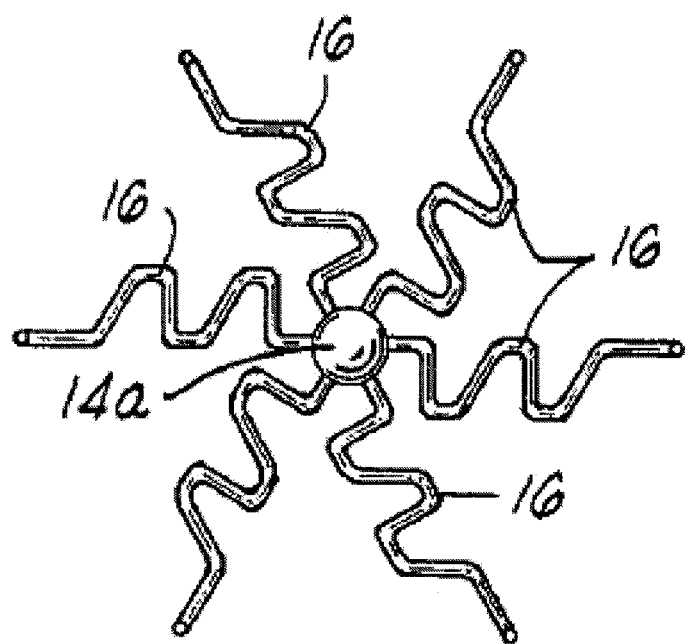
FIG. 10 is an end view of the filter as it appears looking toward the apical hub forming a part of the filter.

FIG. 9 is a view of an IVC filter having an improved echogenic characteristic. A filter constructed in accordance with the invention is illustrated in FIG. 9 as it appears when it is in operative position within a large blood vessel, such as the vena cava. The filter is designated generally by reference numeral 10, and the wall of the blood vessel in which it is located is designated by reference numeral 12. FIG. 10 is an end view of the filter in FIG. 9.

The filter 10 includes an apical hub 14 of overall egg-shaped or tear drop configuration and which has a generally hemispherically shaped end portion 14*a*. This construction avoids impalement of the filter on the blood vessel walls during emplacement, and also avoids irritation or scratching of the blood vessel during insertion of the filter. The apical hub 14 is drilled for the reception of the end portions of a plurality of legs as hereinafter described.

The filter 10 includes a plurality of elongated legs 16 which are, in some embodiments, of equal length and are identically configured to each other. In one aspect, the legs 16 are collectively arrayed in a conical geometric configuration so that the legs converge to the apical hub 14, and are symmetrically spaced about a central axis extending through the hub. Each of the legs is of equal diameter over its entire length and is made of a relatively resilient material, such as tempered stainless steel wire or the like. The legs may be coated with a polymeric, synthetic resin material having anti-thrombogenic properties. In the embodiment of the filter illustrated, six of the legs 16 are provided, and since each of these legs is identical to every other leg, only one of the legs will be described in greater detail.

Figure 11:
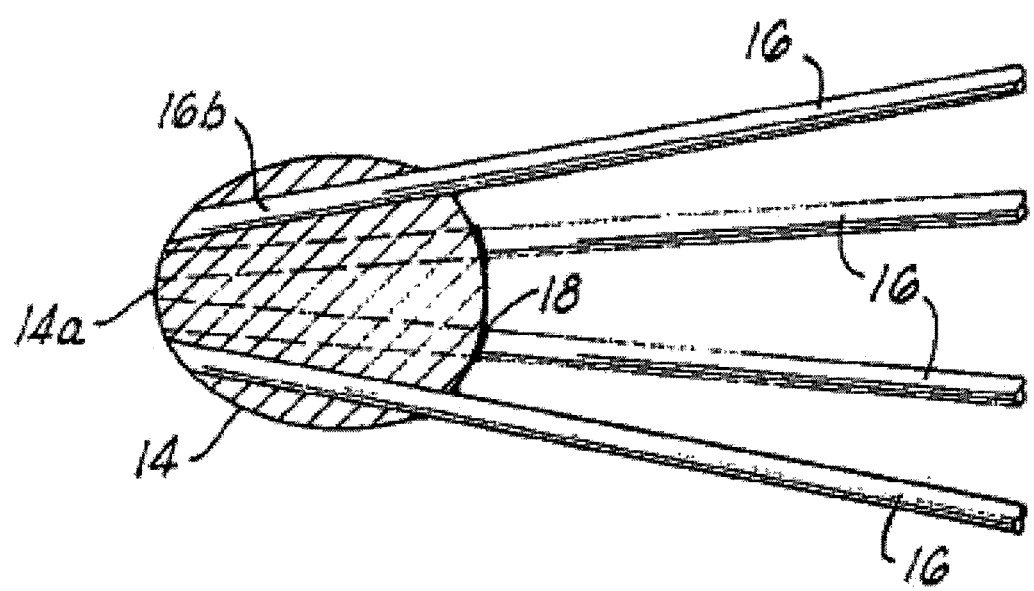
FIG. 11 is a sectional view through the center of the apical hub forming a part of the filter, and illustrating the manner in which the legs of the filter are positioned in the apical hub and are retained therein.

At its outer end, or end which is distally located with respect to the apical hub 14, each leg is reversely bent through an angle of more than 90°, and is tapered or sharpened to a point 16*a*. The reverse bend is outwardly in a direction away from the central axis of the conical figure. As depicted in FIG. 11, the end portions of the several legs 16 project into bores formed through the apical hub 14, and are secured in the hub by suitable techniques.

It will be seen in FIG. 9 that when the filter 10 is positioned in the blood vessel, the points 16*a* at the divergent ends of the legs 16 hook into or impale the wall 12 of the blood vessel, but the hooks are not of sufficient size to penetrate or pass through the wall of the blood vessel. It will further be noted by reference to the arrow within the blood vessel in FIG. 9 that when the blood flows in the direction indicated by the arrow, the pressure exerted by the blood on the filter 10, and any embolus which may be entrapped thereby, tends to set the hooks at the divergent ends of the legs 16 into the wall 12 of the blood vessel so that dislodgment of the filter is resisted.

Figure 12:
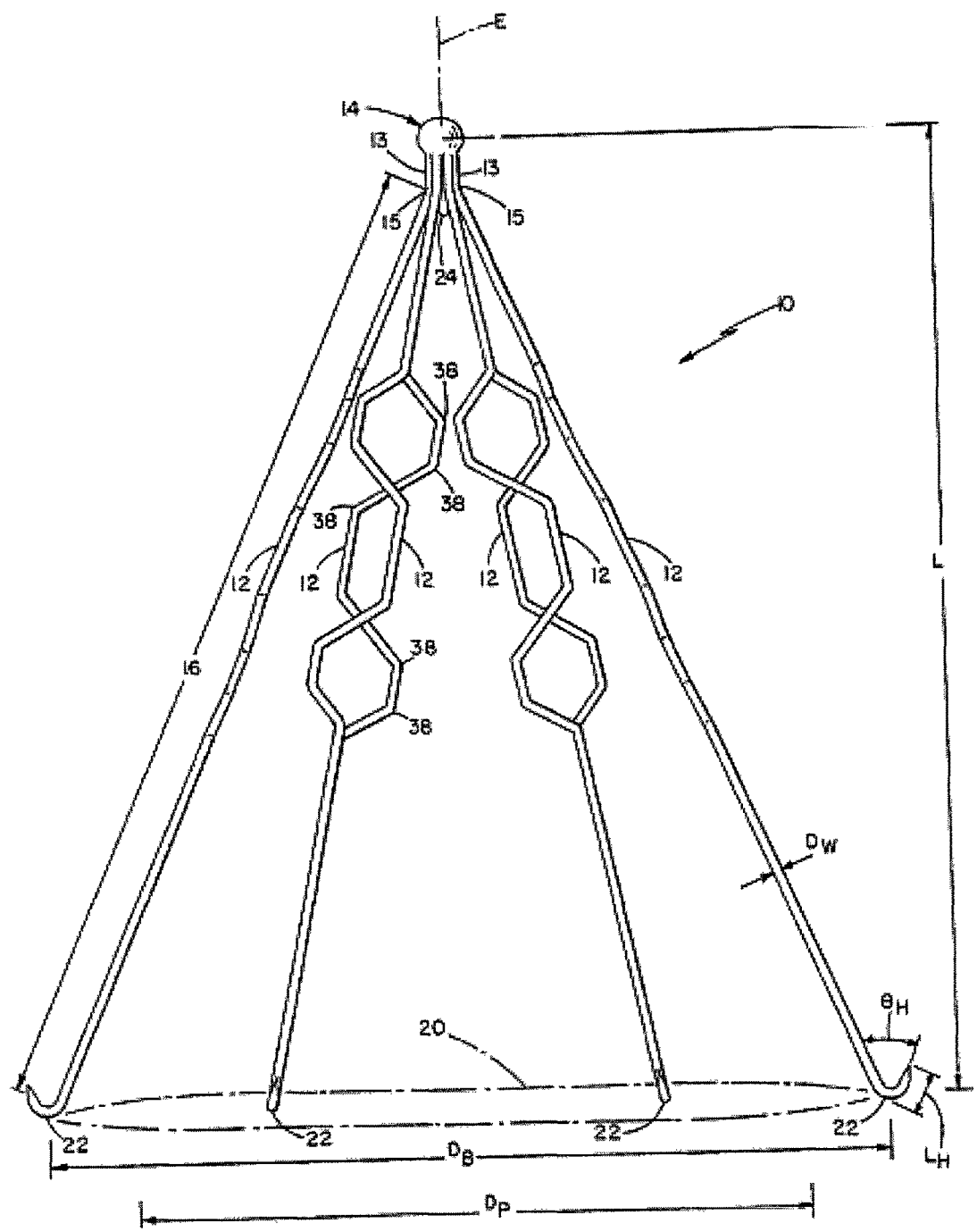
FIG. 12 is a side view of an embodiment of the blood clot filtration device.

FIG. 12 is a view of a breakaway anchor portion of an IVC filter having an improved echogenic characteristic. Referring to FIG. 12, an embodiment of the blood clot filtration device 10 of the invention consists of six legs 12 protruding from a head or nosebead 14. The legs 12, e.g., wire of diameter $D_W$, about 0.018 inch (0.5 mm), each have: a first linear leg portion 13 lying parallel to axis E of the filter, for distance $H_N$, e.g., about 1 mm, a nose bend 15, a second multi angled leg portion 16 of relatively greater length than the first linear leg portion, angling outwardly from the distal end of the first leg portion away from axis E, to define, with other second leg portions, an imaginary cone with base 20, shown as dotted lines; and outwardly directed hooks 22. The second leg portions 16 consist of a series of discrete linear segments arrayed generally tangent to the surface of the imaginary cone in a manner to increase the efficiency of the filtering effect. The diameter of the base of the filter is $D_B$, about 38 mm, and the overall length of the filter is L, about 50 mm. The linear leg portions 13 of all of the legs are closely arranged in a hexagonal pattern about central leg stub or segment 24 and the ends of all of these legs are joined at the apex in proximal head or nose bead 14, formed by fusing the ends of legs 12 and central leg stub 24 together.

The wires forming legs 12 are formed into first linear portion 13, second multi angled portion 16 and hook 22 against a steel guide in such a way that there is an alternating bend circumferentially oriented to produce a characteristic conical structure. Hook 22 has length $L_H$, about 1.8 mm, and is angled at angle $\theta_H$, about 34°. The bends 38 in leg wires 12 are formed by bending the wires at an angle of 130°-150°. Hook 22 is formed mechanically by bending the distal end of wire 12 over a mandrel. Hook 22 is then sharpened on three sides against an abrasive wheel. Nose bend 15 is made to form first linear portion 13 near to bead 14, parallel to axis E of filter 10. The leg 12 then bends slightly outwardly on the major angle of the cone and passes through a series of bends as described above.

The embodiment of the filter described above with regard to FIG. 12 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIG. 12 may be modified according to FIGS. 1-9 above.

Figure 13:
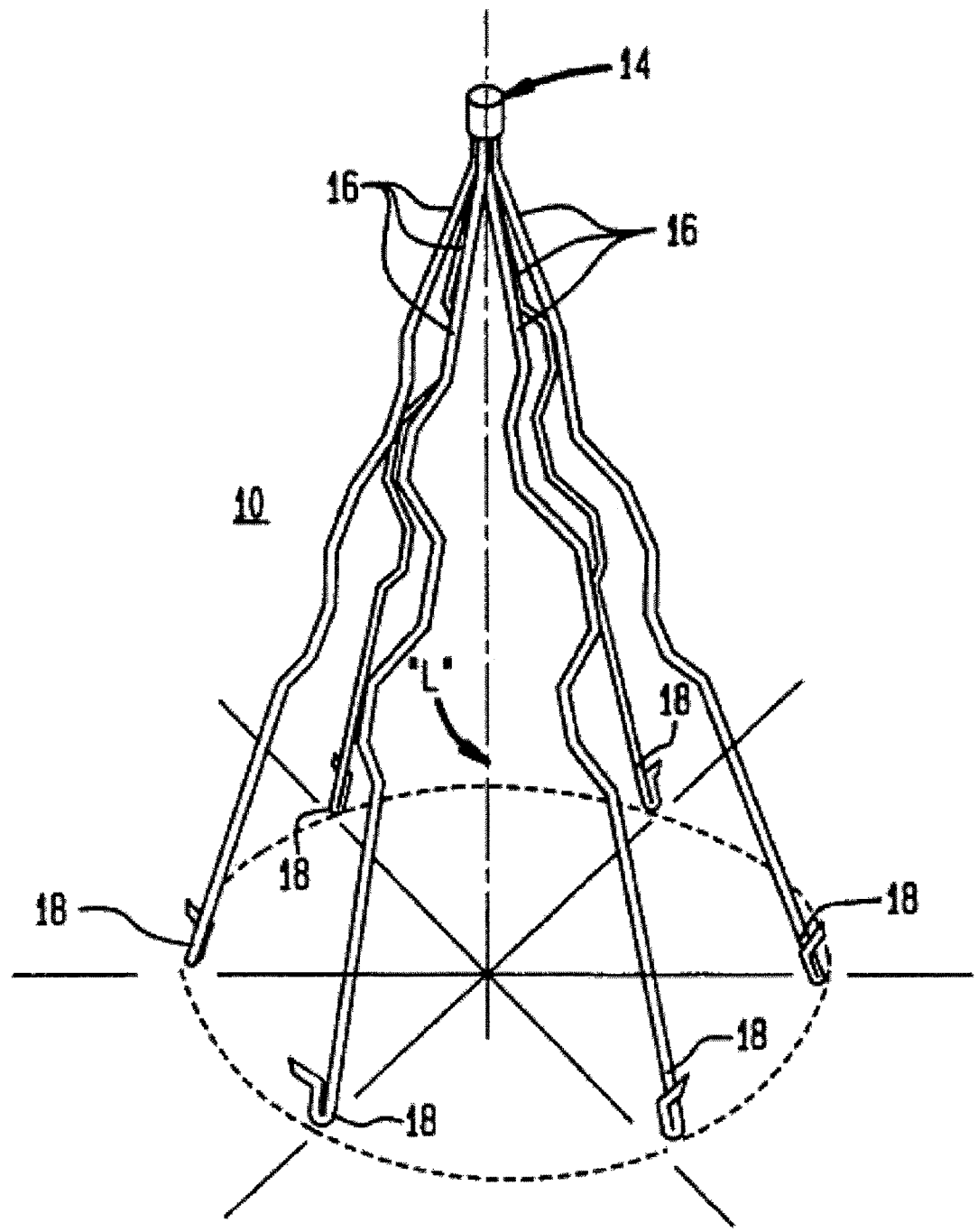
FIG. 13 is a perspective view of a vena cava filter embodiment showing the head and legs thereof.
Figure 14:
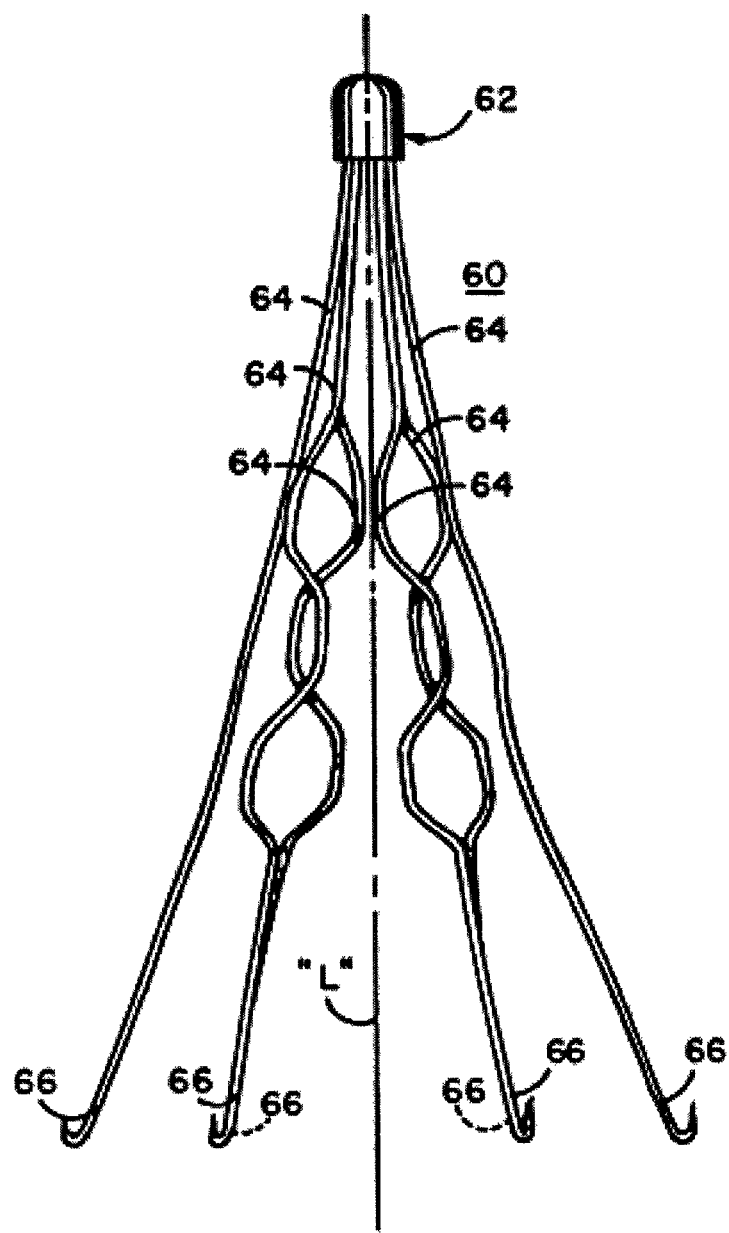
FIG. 14 is a perspective view of a vena cava filter showing the head and legs thereof.

FIGS. 13 and 14 are of an IVC filters having an improved echogenic characteristic. Referring now to FIG. 13, there is shown a first embodiment of a vena cava filter 10 having an apical hub or head 14 of generally cylindrical shape.

The filter 10 includes a plurality of elongated legs 16 which are of equal length, and are preferably identically configured to each other. The legs 16 are collectively arranged in a generally conical geometric configuration so that the legs 16 converge in the apical head 14, and are symmetrically spaced about a central longitudinally disposed axis "L", which is shown extending through the head 14, in FIG. 13. The legs are of equivalent diameter, being about 0.018 inches in diameter fabricated from stainless steel or titanium wire, and are of about 2.02 inches in final length. In the embodiment of the present invention, six legs are provided, however only one will be described in detail.

At its outermost end 18 which is distal with respect to the apical head 14, each leg 16 has a main portion 20 and a reversely bent portion 22 which is bent through an angle of about 180° in the plane which is tangential to the conical configuration of the legs, and is disposed parallel and contiguous to the main portion 20. A pointed tip portion 24 of the leg which comprises a hook, extends generally radially outwardly, away from the main portion 20 at an angle of from 70° to about 90°, which tip portion 24 is shown piercing a cava wall 26.

A further embodiment of a vena cava filter 60 is shown in FIG. 14 having an apical head 62. The filter 60 includes a plurality of elongated legs 64 which are of equal length, and are configured identical to each other. The legs 64 are collectively arranged in a slightly outswept but generally conical configuration so that the legs 64 converge in the head 62, and are symmetrically spaced about a central longitudinally disposed axis "L", which is shown extending through the head 62 in FIG. 13. The legs are about 0.018 inches in diameter fabricated preferably from stainless steel, only one of the legs being described in detail. Each leg has an outermost or distal end 66 with a hook configuration disposed thereon.

A typical leg 64 is each mounted in a bore 68 in the apical head 62, which bore may be parallel to the center line of the filter 60. Each bore 68 receives only about 0.19 inches of the proximalmost end of each leg 64. When all the legs 64 are filling their proper respective bores 68, they are preferably welded therein. Each leg 64, in addition to having a plurality of U-shaped bends 70, disposed in the plane tangential to the cone defined by the legs 64, and intermediate their proximal and distal ends, as recited in the aforementioned incorporated patent, has a first slight bend 72 having a radius of curvature RI of about 1.4 inches arranged immediately adjacent the apical head 62, to cause the leg(s) 64 to flare radially outwardly about 18 degrees, thus defining their cone shaped configuration. This flare permits the filter 60 to have enough elastic recoil to assume its general conical configuration, which is desirable to permit the filtration of blood clots while still allowing blood to flow around the captured clots, thus promoting dissolution of any clot and maintenance of vessel patency. The filter 60 with this flare can be passed through small delivery carriers without exceeding the elastic limit of the stainless steel filter legs 64.

The apical head 62 on the filter 60 has a central cylindrically shaped bore 80 which is adapted to receive inself aligning engagement, a guidewire (not shown). The bore 80 critically has its cylindrical portion which is in axial alignment with the longitudinal center line "L" of the filter 60. Each end of the bore 80 has a tapered counterbore 82 to permit access of a guidewire into the bore 82. This permits the filter 60 to be aligned and centered along the axis of a guidewire in a vessel during (and after) filter emplacement therein.

The embodiment of the filter described above with regard to FIGS. 13 and 14 may be modified to be a filter having enhanced echogenic properties characteristics or features.

This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 13 and 14 may be modified according to FIGS. 1-9 above.

Figure 15:
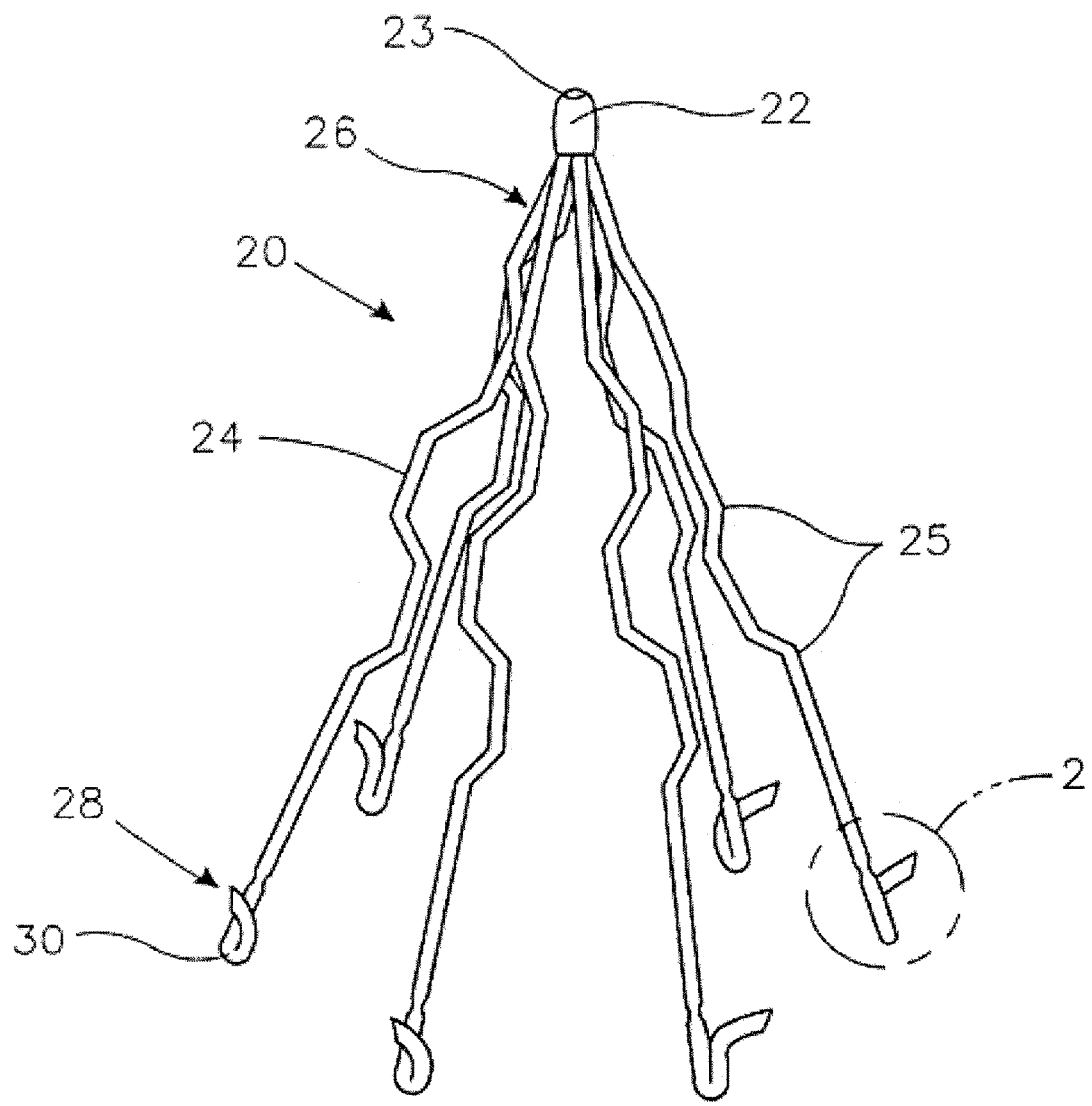
FIG. 15 is a perspective view of a thrombus filter.

FIG. 15 is a view of an IVC filter having an improved echogenic characteristic. FIG. 15 is a perspective view of a thrombus filter 20. Thrombus filter 20 includes a body member 22 and a plurality of elongated struts 24. Struts 24 each have a joined end 26 and a free end 28. Joined end 26 of each strut 24 is fixedly attached to body member 22.

Struts 24 may be fabricated from wire with a circular or rectangular cross section. For example, struts 24 may be comprised of 2 inch lengths of 0.018" diameter wire. Stainless steel, titanium, and nickel-titanium alloys have all been found to be acceptable materials for struts 24. In the embodiment of FIG. 15, a plurality of bends 25 are disposed between free end 28 and fixed end 26 of each strut 24. It should understood that struts 24 may also be straight, or include bends different than those illustrated in FIG. 15, without departing from the spirit of scope of the present invention.

In the embodiment of FIG. 15, body member 22 is generally cylindrical in shape, and includes a bore 23. It should be under stood that other embodiments of body member 22 are possible without departing from the spirit or scope of the present invention.

Struts 24 radiate outwardly from body member 22 such that thrombus filter 20 is generally conical in shape. When thrombus filter 20 is deployed inside a blood vessel, free ends 28 engage the blood vessel wall. Body member 22 is held in a position proximate the center of the blood vessel by the plurality of struts 24 which engage the blood vessel walls with opposing force vectors.

When thrombus filter 20 is disposed in a blood vessel, the conical formation of struts 24 acts to trap, or capture blood clots. The generally conical shape of the formation of struts 24 serves to urge captured blood clots toward the center of the blood flow. The flow of blood around the captured blood clots allows the body's natural lysing process to dissolve the clots.

Figure 16:
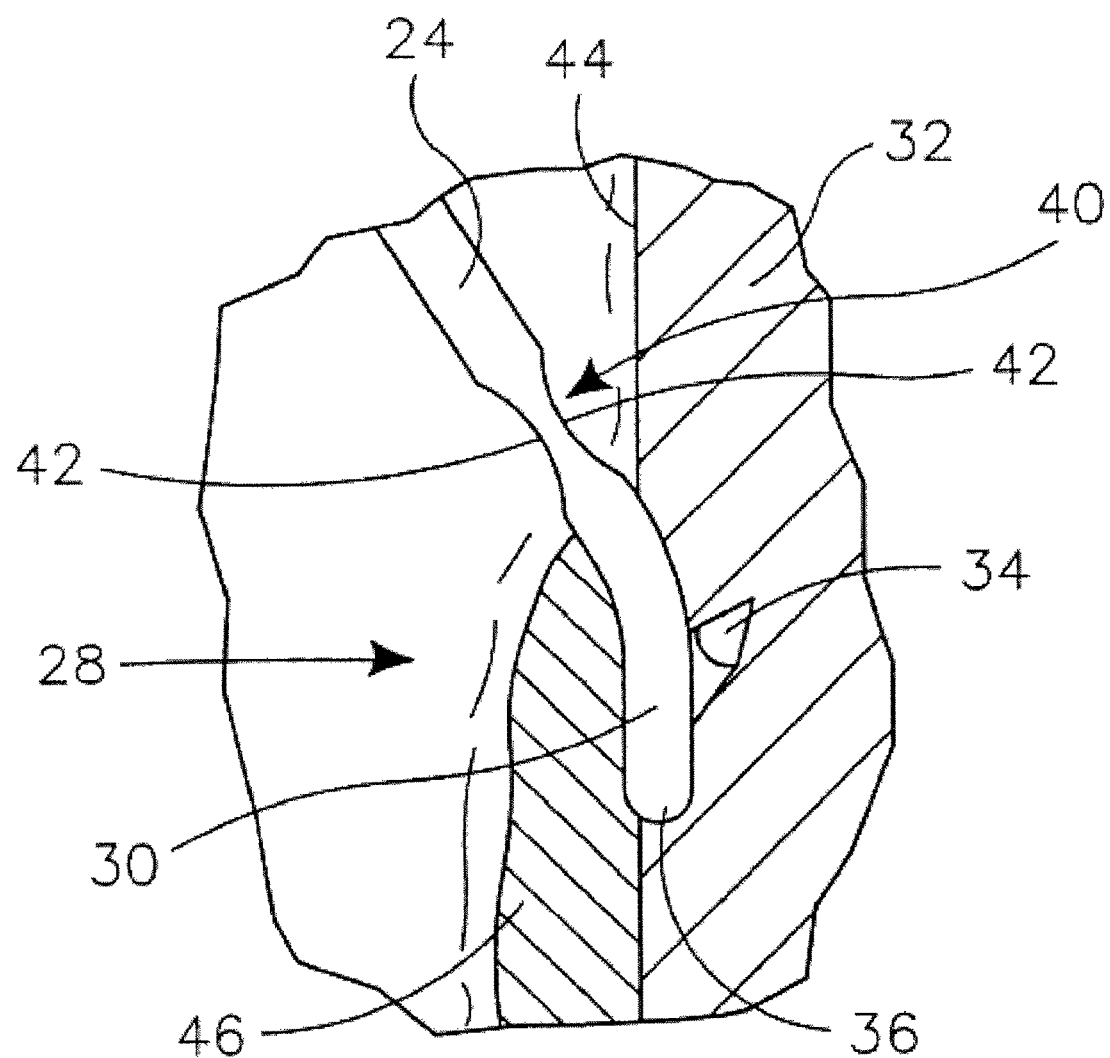
FIG. 16 is a plan view of the anchor portion of a thrombus filter.

To assure firm attachment of thrombus filter 20 to the blood vessel walls, anchor portions 30 may be formed at free ends 28 of struts 24. FIG. 16 illustrates one embodiment of an anchor portion 30 embedded in a vessel wall 32. Anchor portion 30 includes a sharp point 34 and a bend 36. Strut 24 includes a weakened portion 40 disposed proximate free end 28. In the particular embodiment of FIG. 16 weakened portion 40 includes a plurality of divets 42. Divets 42 substantially reduce the cross sectional area of strut 24 at weakened portion 40. Divets 42 may be fabricated by removing material from strut 24 with a removal process such as machining or grinding. Divets 42 may also be fabricated by displacing material with a process such as metal forming or crimping.

Blood vessel wall 32 is lined with a thin inner membrane or intima 44. When anchor portion 30 is embedded in wall 32 it punctures inner membrane 44. The body responds to a puncture of inner membrane 44 with a process known in the art as neointimal hyperplasia. The punctured area of inner membrane 44 is overgrown with a number of new cells. Referring again to FIG. 16, it can be seen that anchor portion 30 of strut 24 is covered with encapsulating cell growth 46.

It is desirable that the thrombus filter of the present invention can be removed using minimally invasive methods without complications due to neointimal hyperplasia encapsulation of anchor portions 30 of struts 24. A process which may be utilized to remove thrombus filter 20 from a blood vessel 90 is schematically represented in FIG. 17.

Figure 17:
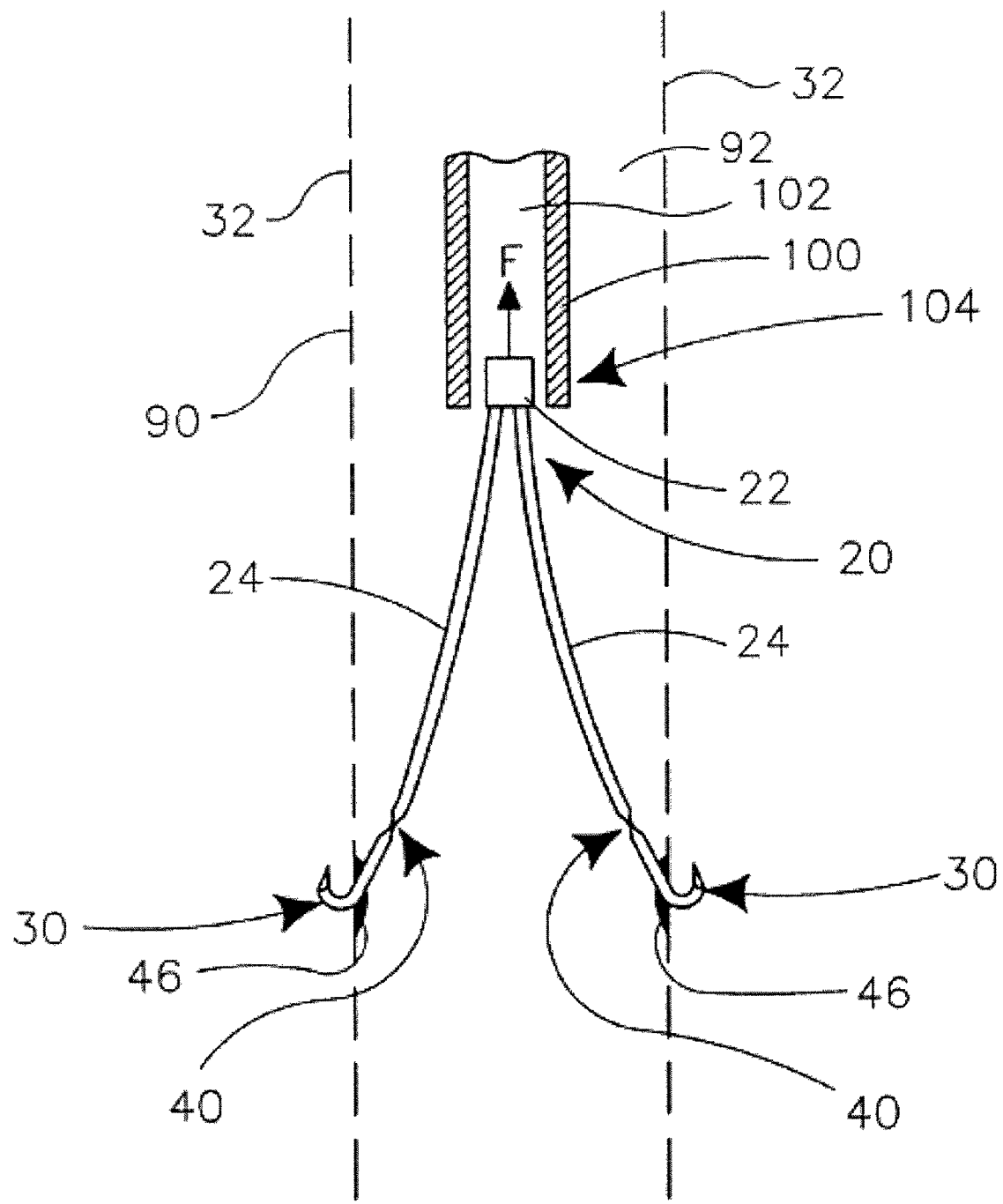
FIG. 17 is a schematic representation of a removal process for use with a thrombus filter.

FIG. 17 schematically illustrates a blood vessel 90 including a lumen 92 and walls 32. Thrombus filter 20 is disposed in lumen 92 of blood vessel 90. Anchor portions 30 of struts 24 are embedded in walls 32 of blood vessel 90. Neointimal hyperplasia has resulted in encapsulating cell growth 46 proximate anchor portions 30 of struts 24.

A removal catheter 100 with a lumen 102 and a distal end 104 is also disposed in lumen 92 of blood vessel 90. Removal catheter 100 enters the patient's vascular system at a point which is readily accessible to the physician. Once in the vascular system, catheter 100 is urged forward until distal end 104 is proximate thrombus filter 20. For example, if thrombus filter 20 is located in the inferior vena cava of a patient's vascular system, removal catheter 100 may enter the vascular system at the femoral vein. Alternately, if thrombus filter 20 is located in the superior vena cava of a patient's vascular system, removal catheter 100 may enter the vascular system at the jugular vein. In either case, the filter removal procedure can be minimally invasive, and not require general anesthesia.

Distal end 104 of removal catheter 100 is urged forward so that body member 22 of thrombus filter 20 is disposed inside lumen 102 of removal catheter 100. A force F is applied to thrombus filter 20 urging body member 22 further into lumen 102 of removal catheter 100. The magnitude of force F is of sufficient magnitude to break struts 24 at weakened portions 40. When struts 24 are broken at weakened portions 40 thrombus filter 20 including struts 24 may be pulled into lumen 102 of removal catheter 100. Removal catheter 100 may then be removed from the body of the patient by withdrawing removal catheter 100 from blood vessel 90. Thus, thrombus filter 20 is removed from blood vessel 100 but anchor members 30 remain attached to walls 32 by encapsulating cell growth 46.

Figure 18:
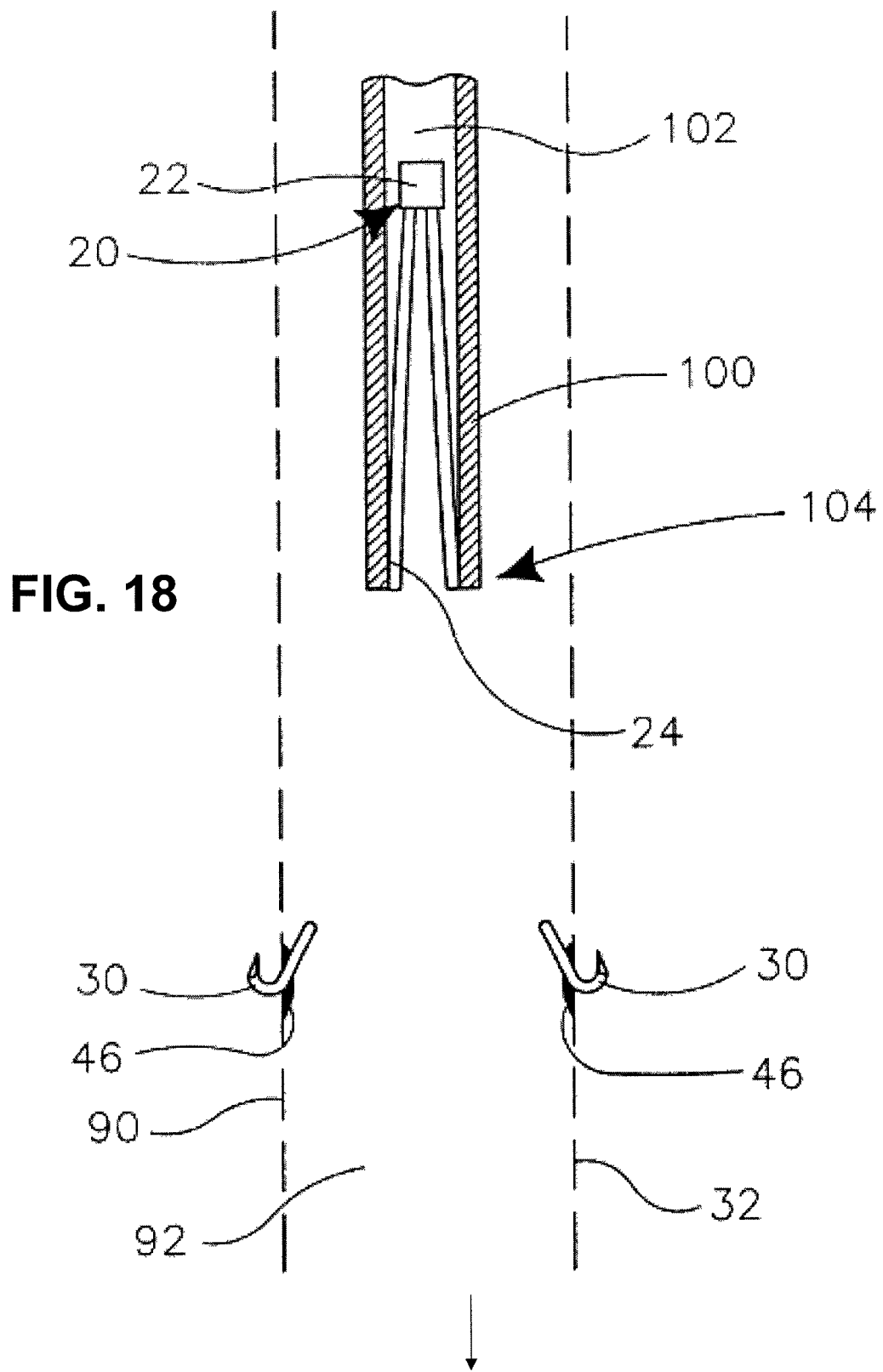
FIG. 18 is a schematic representation of a thrombus filter drawn into the lumen of a removal catheter.

FIG. 18 is a schematic representation of thrombus filter 20 after it has been pulled into lumen 112 of retrieval catheter 110. As may be seen in FIG. 18, pulling thrombus filter 20 into lumen 112 of retrieval catheter 110 causes struts 24 to collapse. When struts 24 are collapsed, retrieval catheter 110 may be withdrawn from blood vessel 100. As can also be seen in FIG. 18, anchor members 30 remain fixed in the walls of blood vessel 100, retained by encapsulating cell growth 46.

Force F may be applied to thrombus filter 20 using a variety of methods. For example, the pulling of thrombus filter 20 into lumen 112 of retrieval catheter 110 may be accomplished with a retrieval wire including a hook. The retrieval wire may pass through bore 23 of body member 22. With the retrieval wire disposed in bore 23 of body member 22, the hook may engage body member 22 so that a pull force can be applied to thrombus filter 20.

Struts 24 may also be intentionally broken at weakened portions 40 by repeatedly deflecting struts 24 to induce fatigue cracking at weakened portions 40. The magnitude of the force required for this removal method is less than the magnitude of force required to break struts 24 without fatigue cracking.

A number of methods may be used to deflect struts 24. First, a pull force may be applied to thrombus filter 10 as shown in FIG. 17. Applying a pull force to thrombus filter 20 deflects blood vessel walls 32 and struts 24. When the pull force is released, blood vessel walls 32 and struts 24 deflect a second time in returning to an unstressed position. Pulling force F may be applied and released repeatedly to induce fatigue cracking at weakened areas 40. It should be noted that the pull force applied when using this removal method is not sufficient to break struts 24 at the outset. However, multiple applications of force F cause fatigue cracks to grow at weakened areas 40. As described above the cross-sectional area of struts 24 is reduced at weakened areas 40 by slots, holes, and the like. The cross-sectional area of struts 24 is further reduced by fatigue cracking due to repeated applications of force F. After multiple applications of force F, the cross-sectional area of struts 24 at weakened areas 40 will be small enough that force F alone is sufficient to break struts 24 at weakened areas 40.

The embodiment of the filters described above with regard to FIGS. 15-18 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 15-18 may be modified according to FIGS. 1-9 above.

Figure 19:
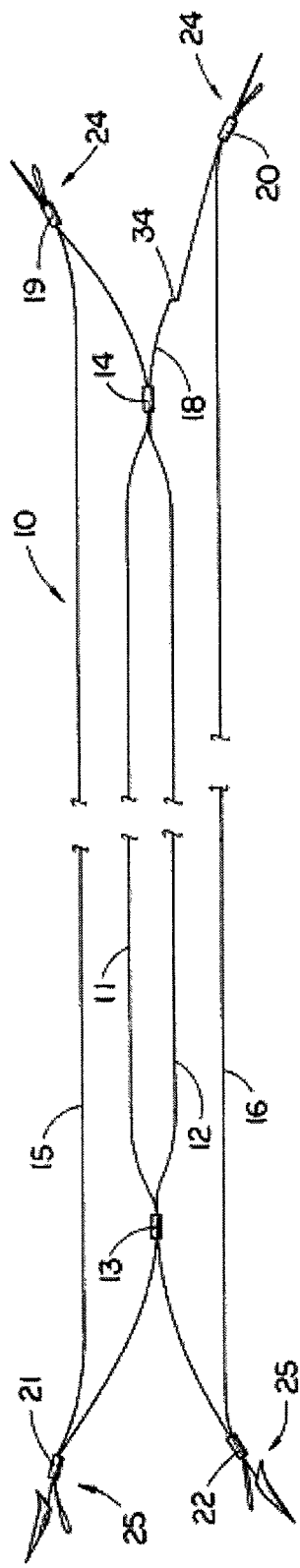
FIG. 19 is a fragmentary elevation view of the blood clot filter embodiment in a totally straightened position.
Figure 20:
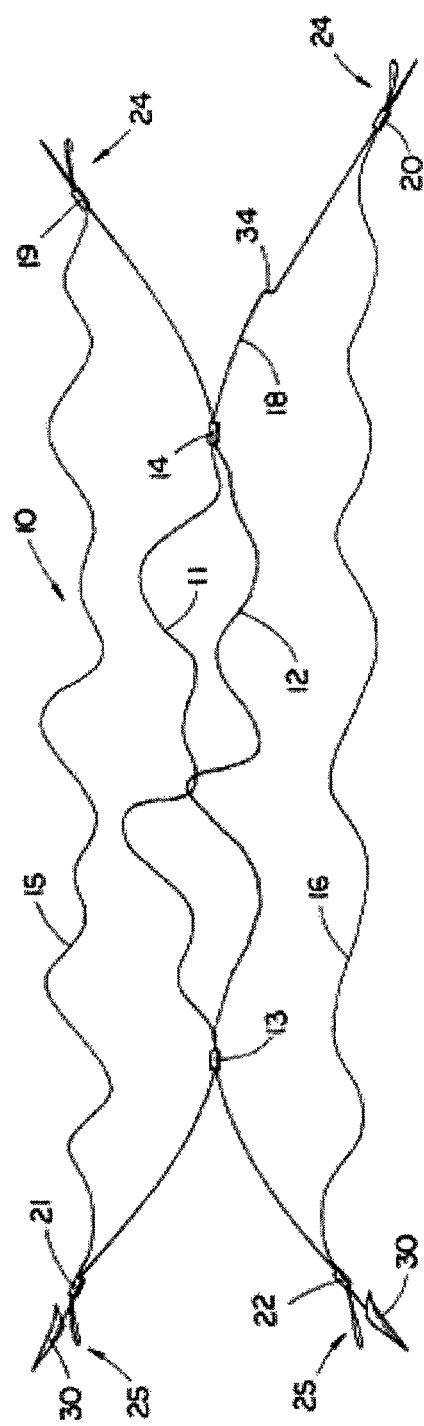
FIG. 20 is an elevation view of the blood clot filter in a partially straightened position.

FIG. 19 is a view of an IVC filter having an improved echogenic characteristic. FIGS. 19 and 20 show a blood clot filter of the clot filter assembly designated at 10. Filter 10 is shown in a totally straightened position in FIG. 19 with its wire strands slightly spaced apart so that the construction of filter 10 may be more clearly seen. FIG. 20 shows filter 10 in a partially straightened but also somewhat curled position. It should be understood that filter 10 would normally assume the shape of a curly wire mesh unless external forces are employed to straighten the wire strands. It is also to be understood that filter 10 would be provided to the physician in a prepackaged assembly additionally including a cartridge catheter and a wire guide handle, both of which will be more fully described herein.

Filter 10 includes six strands of stainless steel wire which are connected to each other in the following manner. Innermost strands 11 and 12 are mutually attached at both ends by crimps 13 and 14. Innermost strands 11 and 12 are approximately 25 centimeters in length and are made from 0.007 inch diameter coil wire. Outermost strands 15 and 16 are located oppositely of innermost strands 11 and 12 and each connected thereto at both ends by wire strands 17 and 18. Outermost strands 15 and 16 are approximately 38 centimeters in length and are made from 0.007 inch diameter coil wire. Wire strand 17 serves to connect outermost strands 15 and 16 with innermost strands 11 and 12 at the distal end of filter 10. In a similar manner, wire strand 18 connects outermost strands 15 and 16 with innermost strands 11 and 12 at the proximal end of filter 10. Wire strand 17 is secured to outermost strands 15 and 16 by crimps 21 and 22, respectively and to innermost strands 11 and 12 by crimp 13. In a similar fashion, wire strand 18 is secured to outermost strands 15 and 16 by crimps 19 and 20, respectively, and to innermost strands 11 and 12 by crimp 14. Wire strands 17 and 18 are approximately 10 centimeters in length and are made from 0.010 inch diameter stainless steel coil wire. Crimps 19-22 are made from 3 mm, of 22 GTW cannula while crimps 13 and 14 are made from 3 mm, lengths of 19.5 GTW cannula. Innermost strands 11 and 12, and outermost strands 15 and 16 are made from a shape memory material, such as spring temper stainless steel.

During manufacture, wire strands 11, 12, 15 and 16 are curled in different directions and wadded together to form a curly wire mesh. Because of their shaped memory construction, innermost strands 11 and 12 and outermost strands 15 and 16 may be straightened out at their ends substantially as shown in FIG. 19 for loading into the lumen of a Teflon angiography catheter cartridge. It may be noted that once loaded within the catheter, the spring bias inherent within the wire strands will cause some curling thereof. Further curling is, of course, restrained by the intimal wall of the catheter cartridge. Thus, it is the spring bias inherent in the shape memory construction which allows filter 10 to expand radially outward as innermost wire strands 11 and 12 and outermost wire strands 15 and 16 contract along their lengths upon insertion in a body blood vessel, as will be more fully explained herein.

Anchoring filter 10 within a body blood vessel, such as the inferior vena cava, is generally provided by fixation elements at 24 and 25, the details of their construction being more clearly understood by reference to FIG. 20. It is to be understood that anchor 24 is located at the rearward end of both wire strands 15 and 16, while anchor 25 is located at the forward end of both wire strands 15 and 16. Anchor 24 differs from anchor 25 due to the presence of a barb 30 whose purpose will become fully apparent hereinafter. The anchor 24 and 25 at the ends of outermost wire strand 15 are longitudinally staggered from the corresponding anchor 24 and 25 at the ends of outermost wire strand 16. This permits the easy loading of filter 10 within the lumen of a catheter cartridge such as will be more fully described herein.

Referring particularly to FIG. 20, the details of construction of the rearward anchoring means 24 will now be described. It is to be understood that while only the rearward anchor 24 at the end of outermost wire strand 15 is described, the rearward anchor means 24 at the end of outermost wire strand 16 is of a similar construction. It is seen that rearward anchor means 24 includes a length 26 of outermost wire strand 15 located at the rearward end thereof. Length 26 is approximately one centimeter in length and has a sharp end point 27 which is meant to enter the wall of a blood vessel. In order to prevent too deep penetration of anchor 24 through the blood vessel, a loop 28 of wire formed from wire strand 18 is positioned adjacent length 26. Loop 28 extends approximately 7 mm along length 26, crimp 19 serving to secure the end of loop 28.

It is to be understood that there are two forward anchor 25 at the forward end of filter 10. As previously mentioned, forward anchor 25 is of a similar construction to anchor 24 except that a barb 30 is received over the end length of wire corresponding to length 26 of anchor 24. The purpose of barb 30 is to provide a more secure anchor at the downstream end of filter 10 and thereby ensure long term patency of the filter. Barbs 30 are secured to the forward ends of the outer most wire strands 15 and 16 by soldering. Each of the barbs 30 have a lancet beveled portion 31 which faces outwards of filter 10 and a hooked portion 32 at the inwards facing end. Hooked portion 32 serves to prevent barb 30 from becoming dislodged from the body blood vessel once penetration thereof has been made. Each of the barbs 30 is constructed from 6 mm, to 0.028 inch diameter cannula.

Figure 21:
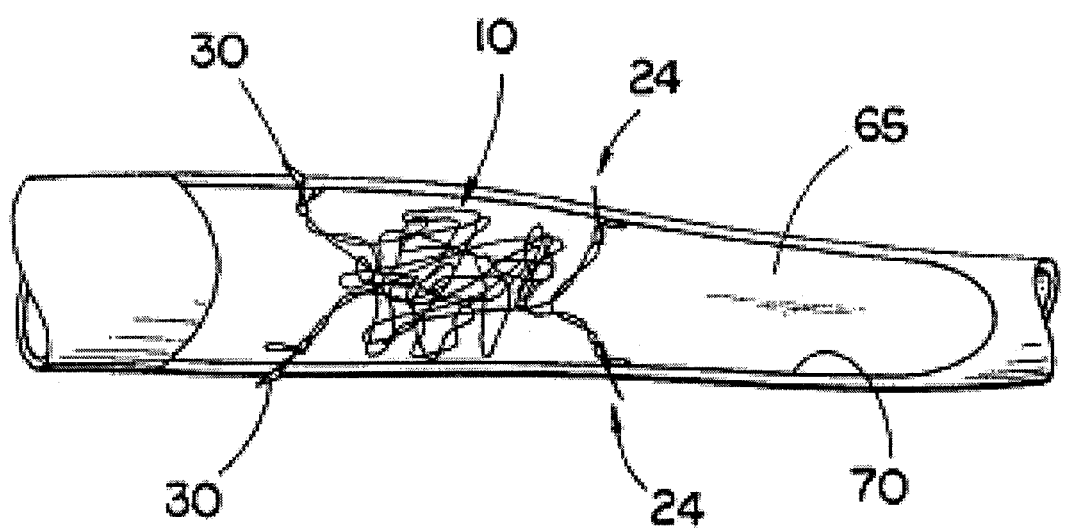
FIG. 21 is a perspective view of a portion of the inferior vena cava and having a section removed to show the configuration of the blood clot filter in its implanted and anchored position within the inferior vena cava.

FIG. 21 show filter 10 in its longitudinally contracted and radially expanded position within the inferior vena cava of a human body. It is to be noted that in this position filter 10 is in the shape of a curly wire mesh with spaces therethrough no larger than 3-4 mm. Also, due to the relatively small diameters of the wire strands, filter 10 occupies only a minimal portion of the cross-sectional area of the blood vessel passageway. Thus, filter 10 does not substantially occlude the blood vessel passageway. Also, barbs 30 extend into the intimal wall of the inferior vena cava in such fashion so as to firmly anchor filter 10, thereby ensuring long term patency.

In addition to the anchoring points at barbs 30, FIG. 21 also shows filter 10 in urging contact with the intimal wall 70 of the inferior vena cava 65 at innumerable other points along the lengths of various portions of the wire strands of filter 10. Initially, these points of urging contact do not provide sufficient anchoring to ensure patency of filter 10, thus requiring the anchoring provided by barbs 30. However, after several weeks endothelization and fibrotic encasement occurs at the points where the wire mesh of filter 10 abuts the intimal wall of the inferior vena cava, and the likelihood of permanent patency is thereafter greatly increased.

Figure 22:
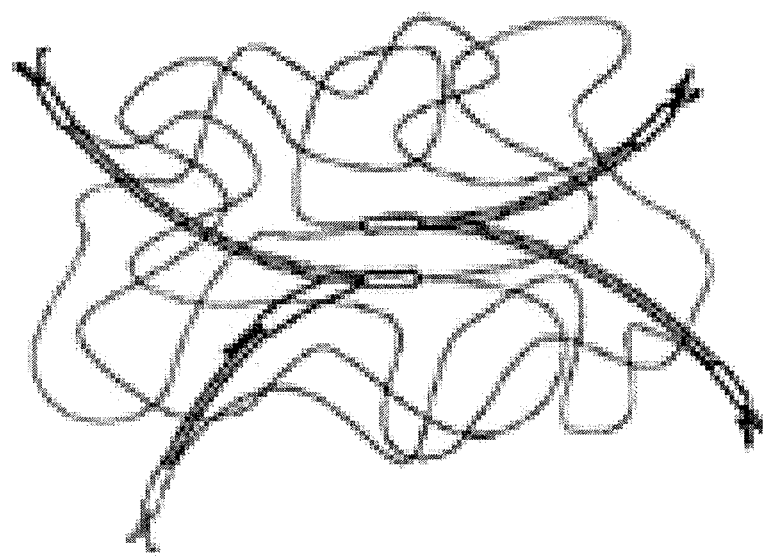
FIG. 22 is a perspective view of an alternative blood clot filter having two V-shaped struts and a tangle of fine wires.

FIG. 22 is an alternative embodiment similar to FIG. 20. FIG. 22 includes 2 V-shaped struts supporting the fine wires as described above.

The embodiment of the filter described above with regard to FIGS. 19-22 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 19-22 may be modified according to FIGS. 1-9 above.

Figure 23:
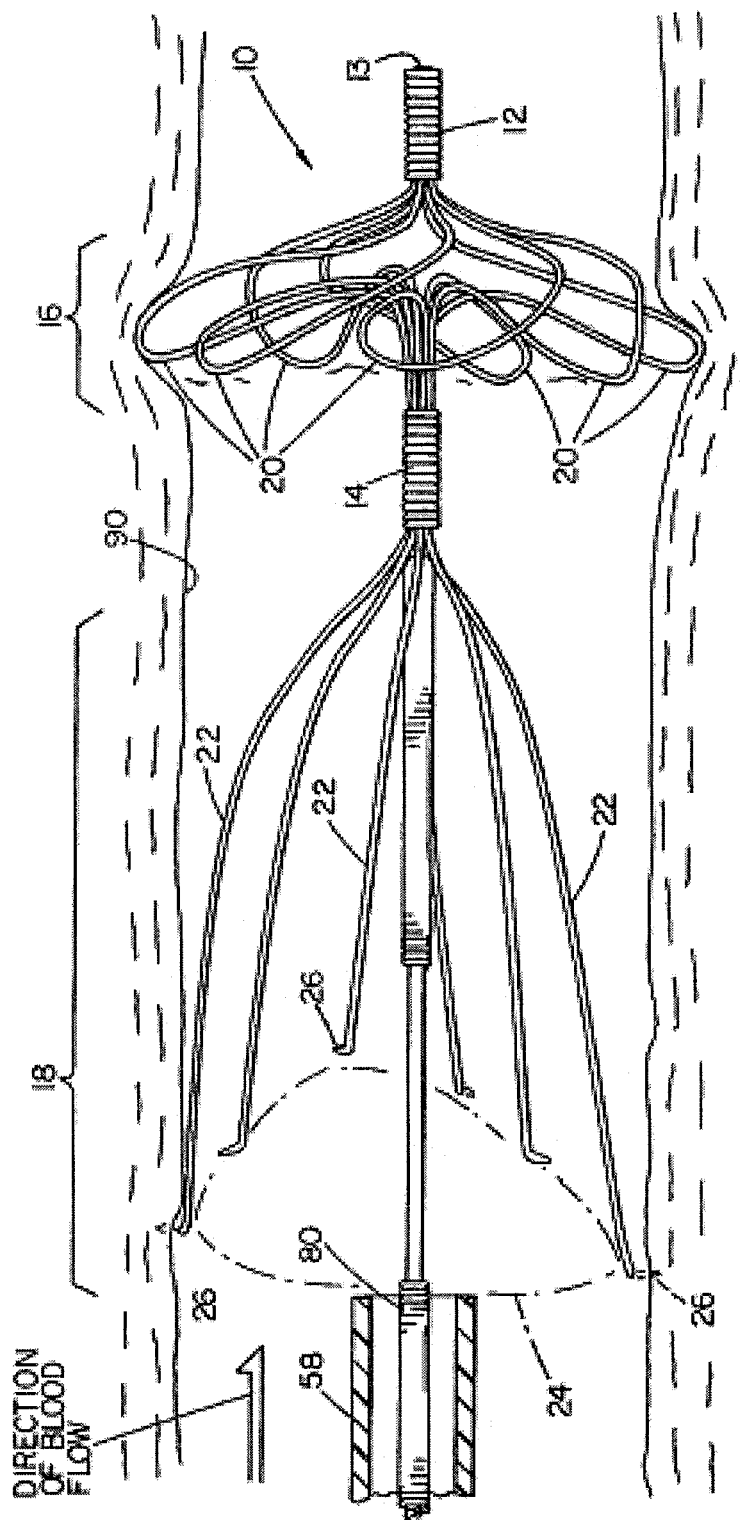
FIG. 23 is a view of a filter in place in a vein.

FIG. 23 is a view of an IVC filter having an improved echogenic characteristic. The filter 10 in FIG. 23 is made up of a set of seven wires. Six of these are approximately three inches in length when fully extended. The seventh is approximately two inches in length when fully extended. The wires are held together by two small sleeves or coils 12 and 14 of the same material, each coil being spot welded to hold it in place and approximately one-quarter of an inch in length; coil 12 is adjacent the tip 13 of the seven wires, and coil 14 is approximately two inches from tip 13 when the wires are fully extended. In the low temperature phase of the material the set of wires can be straightened and held in a straight form that can pass through a length of fine plastic tubing with an internal diameter of approximately 2 mm (#8 French catheter).

In its normal expanded configuration or performed filtering shape, filter 10 is a double filter, having a first filter basket 16 and a second filter basket 18. The two filter baskets provide peripheral portions which engage the inner wall of the vein at two longitudinally spaced locations. The two filter baskets are generally symmetrical about a longitudinal axis passing through filter tip 13.

The mesh of first filter basket 16 is formed from the sections of wires between the two quarter-inch coils 12 and 14. The mesh is made up of a series of seven overlapping loops 20 arranged to form a rosette approximately 25 mm in diameter. The loops are angled slightly relative to the long axis of filter 10 and this angle can be varied to accommodate somewhat smaller diameters if the device is to be constrained in a tube of less than 25 mm in caliber. The loops 20 effectively divide the cross-sectional area to be filtered. The rosette formed by loops 20 can expand or be compressed to fit various sizes of vein. The peripheral portions or tips of the loops 20 press outwardly against the inner wall of the vein, although without becoming imbedded in the vein; loops 20 thereby help to keep filter 10 in place. First filter basket 16 is convex relative to filter tip 13.

The mesh of second filter basket 18 is formed by the six circumferentially spaced free wire ends or legs 22, which tilt and bow outwardly of the long axis of filter 10. The seventh wire terminates within sleeve 14 for use in inserting filter 20. The six free ends or legs 22 that extend beyond the second quarter inch coil 14 diverge so that their tips form a circle 24 of approximately 40 mm in diameter at their maximum divergence. Each leg is also bowed outwardly slightly. The legs serve to orient the device relative to the long axis of the vena cava. Second filter basket 18 is convex relative to filter tip 13.

In another alternative embodiment the legs are tilted outwardly but are not formed with a bow. In such an embodiment, second filter basket 18 opens away from filter tip 13 without being strictly convex.

Each free end of leg 22 is bent sharply outward at about a right angle to form a hook 26 of approximately 1.5 mm in length. The hooks are intended to engage the wall of the vena cava to prevent migration proximally or distally.

The six legs 22 are of slightly different lengths to permit good packing within the delivery device, as will be described; if legs 22 are all of a single length, the hooks may interfere with one another, so that the filter does not expand properly when delivered into the vein.

Figure 24:
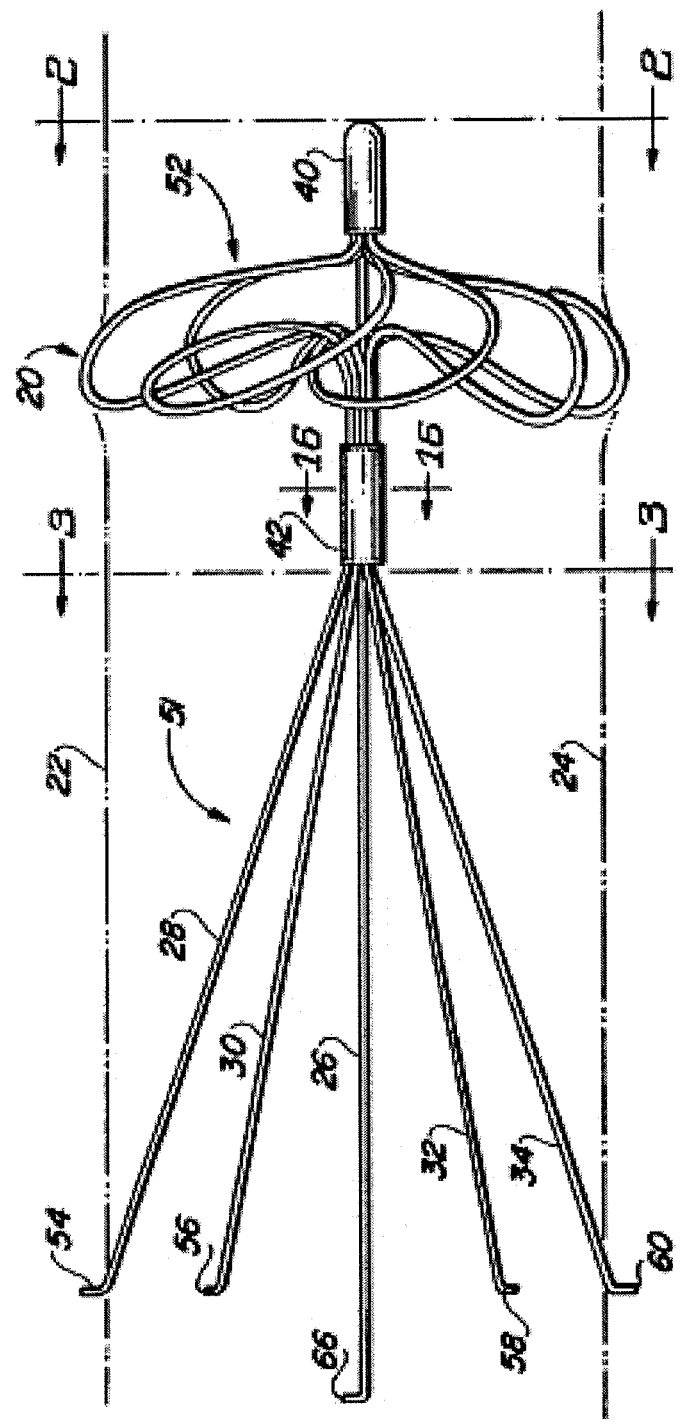
FIG. 24 is a side view of a blood clot filter.

FIG. 24 is a view of an IVC filter having an improved echogenic characteristic. In FIG. 16, a blood clot filter of the type intended for percutaneous introduction and delivery using a transfemoral approach is shown and is designated generally by reference numeral 20. Within FIG. 16, dashed lines 22 and 24 indicate the outline of an interior wall of a blood vessel, such as the inferior vena cava. Blood clot filter 20 consists essentially of a central core wire 26 which extends generally along the central longitudinal axis of blood clot filter 20, as well as six peripheral wires 28, 30, 32, 34, 36 and 38 spaced equiangularly about central core wire 26. Peripheral wires 36 and 38 are hidden from view in FIG. 16 by peripheral wires 30 and 32, respectively.

In FIG. 24, a first connector 40 is shown forming a nose of blood clot filter 20. Connector 40 serves to connect together a first end of each of peripheral wires 28-38, and attaches such peripheral wires about the first end of central core wire 26 at a first connection point. Connector 40 is welded, crimped or otherwise attached to the first end of central core wire 26 and to the first ends of peripheral wires 28-38 so that a fixed connection is achieved between the central core wire and the six peripheral wires.

Still referring to FIG. 24, the six peripheral wires 28-38 are again joined along their central portions by a second connector 42. Connector 42 is in the form of a tubular collar having a central opening defining an interior wall 44. Each of the peripheral wires 28-38 passes through tubular collar 42 and is secured to interior wall 44 thereof, as by welding or by other means of attachment. Thus, second connector 42 serves to connect together peripheral wires 28-38 at a second connection point spaced apart from the first connection point at first connector 40, it will be noted that central core wire 26 passes freely through the interior space defined by tubular collar 42 and the peripheral wire secured therein, thereby allowing second connector 42 to slide along central core wire 26.

The embodiment of the filter described above with regard to FIGS. 23 and 24 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 23 and 24 may be modified according to FIGS. 1-9 above.

Figure 25:
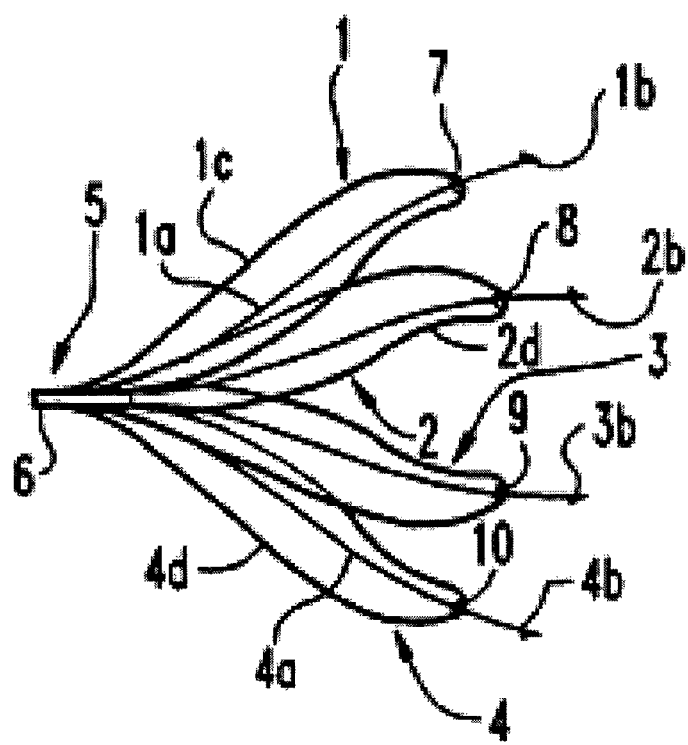
FIG. 25 is an embodiment of a filter in its unfolded state.

FIG. 25 is a view of an IVC filter having an improved echogenic characteristic. The filter in FIG. 25 comprises four legs 1, 2, 3 and 4 diverging from an apical hub 5 at which the legs 1 to 4 are held together by an end ferrule 6 of the kind e.g. disclosed in U.S. Pat. No. 4,619,246, incorporated herein by reference.

Each leg comprises a central element 1a, 2a, 3a, and 4a bent into a smooth quasi-halfsinusoidal form and having a reversely turned anchoring hook 1b, 2b, 3b and 4b at its distal end with respect to hub 5 as well as two symmetrical curved side elements 1c, 2c, 3c and 4c, and 1d, 2d, 3d and 4d extending on either side of the central element.

In the embodiment shown the two side elements of each leg 1 to 4 are formed from one piece of wire the ends of which are held together in hub 5, whereas at the middle of its length the wire piece forms an eyelet 7, 8, 9 and 10 surrounding the central leg element to be freely slidable along a part of the length thereof.

From the unfolded tulip-like configuration illustrated in FIG. 25 the filter may be collapsed into a slender and very narrow bundle of filter elements the cross-sectional dimension of which is approximately equal to the sum of the thicknesses of the central and side elements of all four legs.

The side elements of each leg have a length and curvature such that in the unfolded tulip-like configuration of the filter the maximum distance between the side elements is of the same order as the distance between neighboring side elements of two adjacent legs. Moreover, the length and curvature is preferably chosen such that after insertion into the vena cava inferior the eyelets 7-10 will be positioned substantially at the inner side of the wall of the blood vessel.

As best seen in FIG. 25 the filter according to the invention has in its unfolded state a relatively short axial length of the same order as the diameter of the filter whereby proper arrangements of the filter into the inferior vena cava is facilitated.

The embodiment of the filter described above with regard to FIG. 25 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIG. 25 may be modified according to FIGS. 1-9 above.

Figure 26:
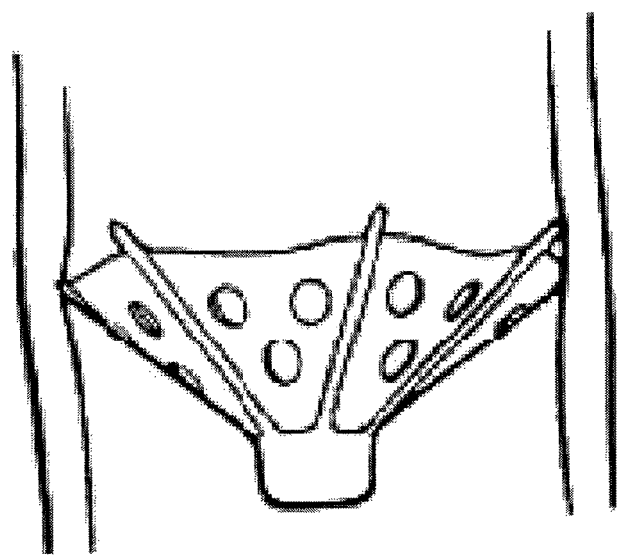
FIG. 26 is a side of the filter in an expanded position.
Figure 27:
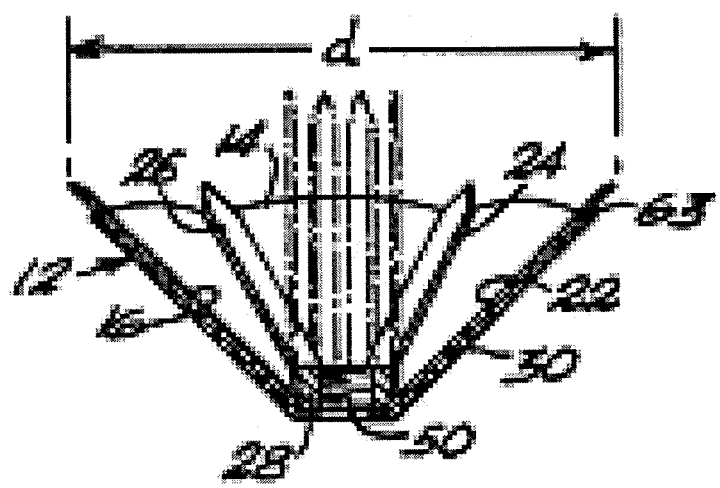
FIG. 27 is a view illustrating the filter by chain dot lines in a collapsed condition.

FIG. 26 shows a filter generally designated by the numeral 12, and in FIG. 27 it is seen to comprise a generally dome-shaped body 14 of open work construction composed of skeletal members such as 16, 18, 20, 22, 24 and 26 which are arranged in a manner somewhat similar to the struts of an open umbrella canopy, and when in the open position shown in FIG. 27, span a distance d greater than that which characterizes the range of diameters commonly encountered in the inferior vena cava. In the preferred embodiment, the six radiating spokes are of collapsible, resilient, alloy material. The inward or converging proximal ends of the spokes or frame members con-verge to a hub 28 and are there united forming the skeletal frame. The distal ends of the struts or spokes all extend somewhat beyond the outer lip or margin of the canopy now to be described, and these ends are preferably sharpened to comprise a holding and gripping means, as will be apparent hereinafter. The canopy portion 30 comprises a suitable filter media of generally sheet form overlaying and being supported on the framework. Preferably, the filtering media includes a plurality of holes in the preferred embodiment, one hole being disposed in the generally triangular portion of the canopy between each of the spokes, and these holes or openings, one of which is designated by the numeral 32 for purposes of clarity, are on the order of about 3 millimeters in diameter and are circular in cross section. The pointed distal ends of the spokes appear as circumferential teeth which extend outwardly of the canopy. The hood or canopy is preferably of a flexible, smooth surfaced material, such as a plastic material, and which provides a smooth surface. For purposes-which will be apparent hereinafter, there is an axial recess 50 in the hub which is threaded.

The embodiment of the filter described above with regard to FIGS. 26 and 27 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b)

formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 26 and 27 may be modified according to FIGS. 1-9 above.

Figure 28:
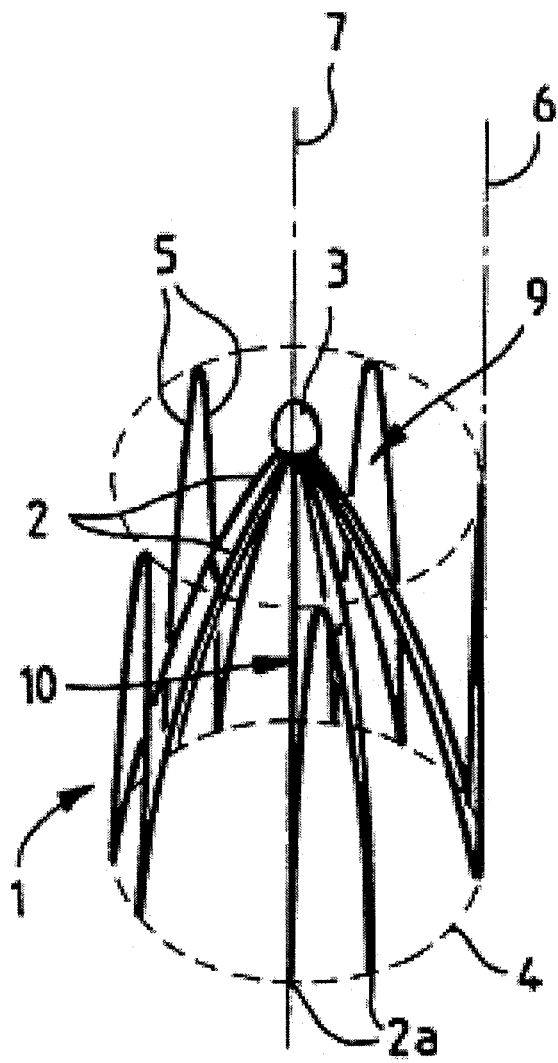
FIG. 28 shows schematically in perspective a filter its unfolded state.

With reference firstly to FIG. 28, there is thus illustrated a filter 1 in the unfolded position consisting of fingers 2, of which there are ten for example, which emerge from a head 3 and which can be unfolded substantially in a generally conical shape of which the opening is marked in dashed lines at 4. Each finger is provided at its free end with a centering and bearing runner 5 which turns substantially behind the head 3; that is, this runner 5 is directed from the end 2a of the fingers towards the closure side of the cone forming the filter. More precisely, if we designate as 6 the cylinder generated by a generating line that is parallel with the axis 7 of the conical shape formed by the filter 1 and moved such that it describes the line 4, the runners 5 are directed such that they are substantially parallel with the wall of the cylinder 6.

In accordance with the invention, the filter fingers consist of flexible wires 8. They may in particular consist of metal wires, for example of a suitable grade of stainless steel. The diameter of the wires may be between 2 and 4 tenths of a millimeter for example 3 or 3.5 tenths of a millimeter.

These fingers are combined in groups of two adjacent fingers by a wire part which is folded in the manner of a hairpin 9 and forms said runners. As a result, the fingers are in the general shape of a clip 10. Advantageously, the filter preferably comprises at least six of the above fingers connected to three wire portions folded in the manner of a pin and distributed in an angular manner so as to ensure that the filter has good axial stability.

Figure 29:
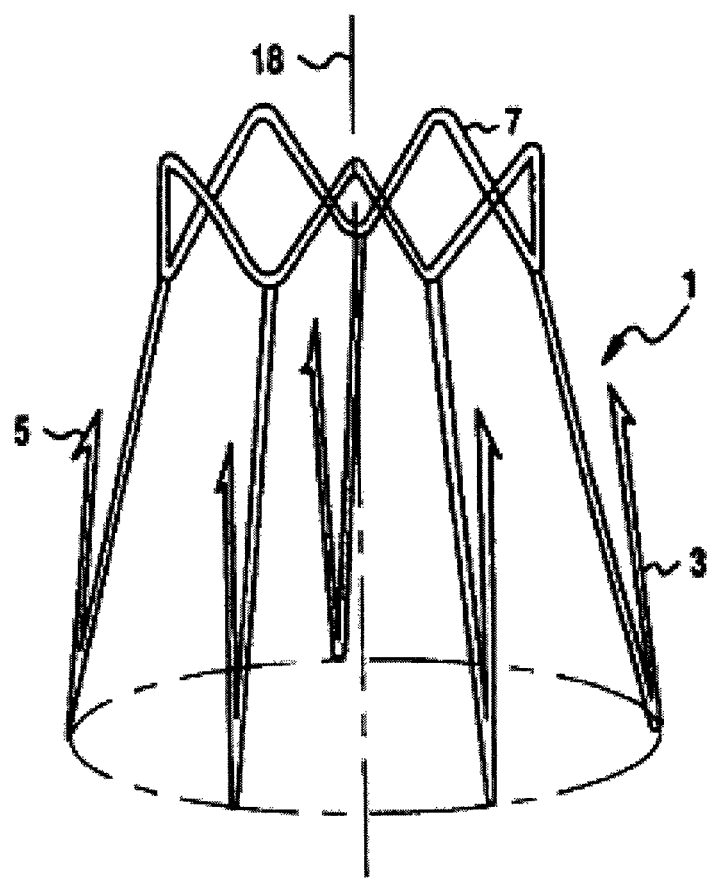
FIG. 29 is an isometric view of a filter.

Referring to FIG. 29, it will be noted that the filter, which is generally indicated 1, comprises a series of elongated branches or legs 3 each of which is substantially "V"-shaped. One of the free ends of each "V" comprises fixation means such as a hook 5 for anchoring the filter to the vessel wall. The other end is connected to a metal thread, which has a succession of corrugations or undulations (such as zig-zags) forming a resilient annular structure 7 of which the central opening has a diameter which can be more or less "constricted" and which is adapted to permit the passage of the temporary filter. The various branches 3 can be produced in the form of fine metal threads and are secured around the annular structure or ring 7 However, the whole of the filter could also be produced in a single metal piece, its structure being obtained by cutting.

In order to be introduced into the vessel, the filter 1 can adopt a constrained state in which the elongated branches or legs 3 are moved close up to the axis 18 of the central opening of the filter until they are substantially parallel thereto. When it is in place in the vessel, the filter adopts a radially expanded state, the branches 3 then moving away from the axis 18 and the hooks 5 anchoring themselves in the vessel wall.

The embodiment of the filter described above with regard to FIGS. 28 and 29 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 28 and 29 may be modified according to FIGS. 1-9 above.

Figure 30:
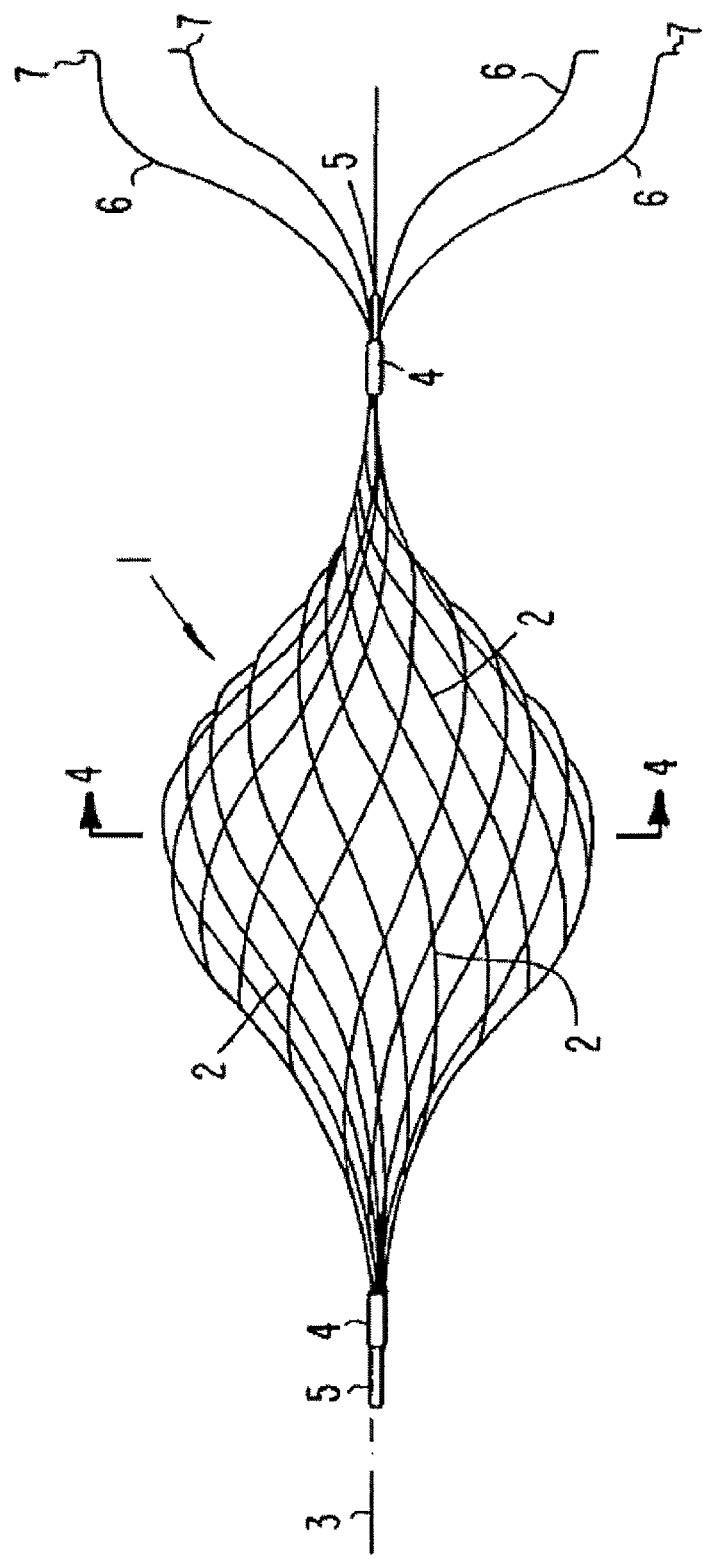
FIG. 30 is an elevation of a vena cava filter shown in its fully expanded state.

In FIG. 30 there is illustrated a vena cava filter comprising a filter basket generally designated by 1 and consisting of a plurality of thin resilient wires 2 of a suitable material, preferably a stainless steel alloy. As illustrated in FIG. 30, basket 1 is generally shaped as an elongate, apertured solid of revolution resulting from the rotation of a sinusoid curve about an axis of rotation indicated in FIG. 30 by a dot-and-dash-line 3, which is tangent to the generatrix at the ends thereof. At each end of the basket proper, the wires are interconnected by means of a short ferrule 4 secured to the wires by any appropriate means, such as brazing.

As shown in FIG. 30 the ratio of the basket length to its maximum diameter is approximately 2. It should be understood that the exact value of this ratio is not critical for the function of the filter basket and in practice it may assume a value between 1.5 and 3, or even higher, although probably the improvement at higher values may be marginal.

As appears from FIG. 30, between the end ferrules 4 each wire 2 follows a helix-like curve, all curves being similar and having the same "hand", in the example right-handed. From one end to the other, each wire 2 is "twisted" approximately 90° about the axis 3.

In FIG. 30 a small, oblong eyelet 5 of wire similar to wires 2 is secured in each ferrule 4 so as to protrude axially from basket 1. By means of either eyelet 5 and a mating hook or other gripping device at the end of an insertion wire, the collapsed filter basket may be pushed or pulled through an inserting catheter, as briefly discussed above.

A plurality of anchoring legs 6, in the example five, are secured in the right-hand ferrule 4 of FIG. 30, from which they extend axially away from basket 1 and outwardly relative to axis 3. The free end of each leg 6 is bent outwardly to form a hook 7 which, when the filter basket has been positioned in a blood vessel, penetrates slightly into the wall of the vessel so as to hold the filter basket in position. Legs 6 will normally be made of the same or a similar material as wires 2 so that they can be readily collapsed to fit within the lumen of the insertion catheter, and spring back to engage the wall of the blood vessel when released from the catheter. The pronounced S-shape of legs 6 in the region immediately inwardly of hooks 7 ensures that when the filter basket moves through the catheter it will be the smooth curved portions of the legs rather than the hooks 7 which contact the catheter wall.

The embodiment of the filter described above with regard to FIG. 30 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIG. 30 may be modified according to FIGS. 1-9 above.

Figure 31:
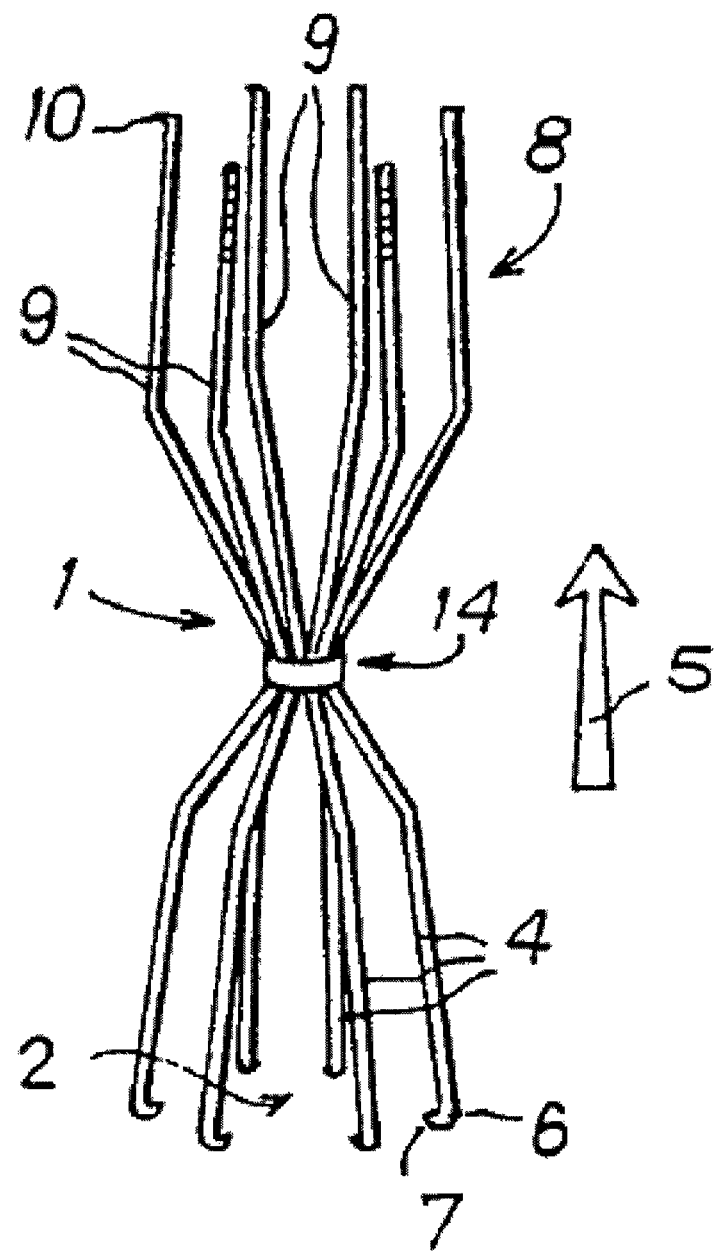
FIG. 31 illustrates an embodiment of a filter, seen in perspective.

Referring now to the drawings, FIG. 31 shows the filter 1 of the present invention which firstly comprises filtering section 2 adapted to open out in the blood vessel 3, particularly the inferior vena cava, when the filter is correctly positioned in the patient.

These filtering section 2 are advantageously constituted by an assembly of flexible filiform elements 4 joined together by one of their ends to form substantially the envelope of a cone, ogive or the like.

In this way, this assembly of filiform filtering elements 4 will be permeable to the blood flow, indicated by arrows 5, but adapted to retain the clots. To that end, it will be disposed in the direction of the blood flow, i.e. the apex of the cone or the like will be directed substantially in the same direction as the blood flow.

By way of example, the flexible rods 4 will be six in number and made of a biocompatible material, such as a suitable metal alloy or plastics material. However, these materials will be chosen for their aptitude to elasticity and to deformation.

In fact, the rods 4 will represent a good flexibility in order, on the one hand, to be folded in a catheter of small dimensions and, on the other hand, to open out correctly in the blood vessel to form a barrage at the latter's dimensions.

Furthermore, the filiform filtering elements 4 will be such that they are non-aggressive with respect to the inner walls of the vessel.

More precisely, as shown in FIG. 31, the rods 4 present at least a slight angle or curve 6, so that their terminal part 7 is in non-aggressive contact with the vessel, when the filtering means are opened out, but so that there is no penetration of the ends of the rods 4 in the wall of the vessel proper.

The embodiment of the filter described above with regard to FIG. 23 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIG. 23 may be modified according to FIGS. 1-9 above.

Figure 32:
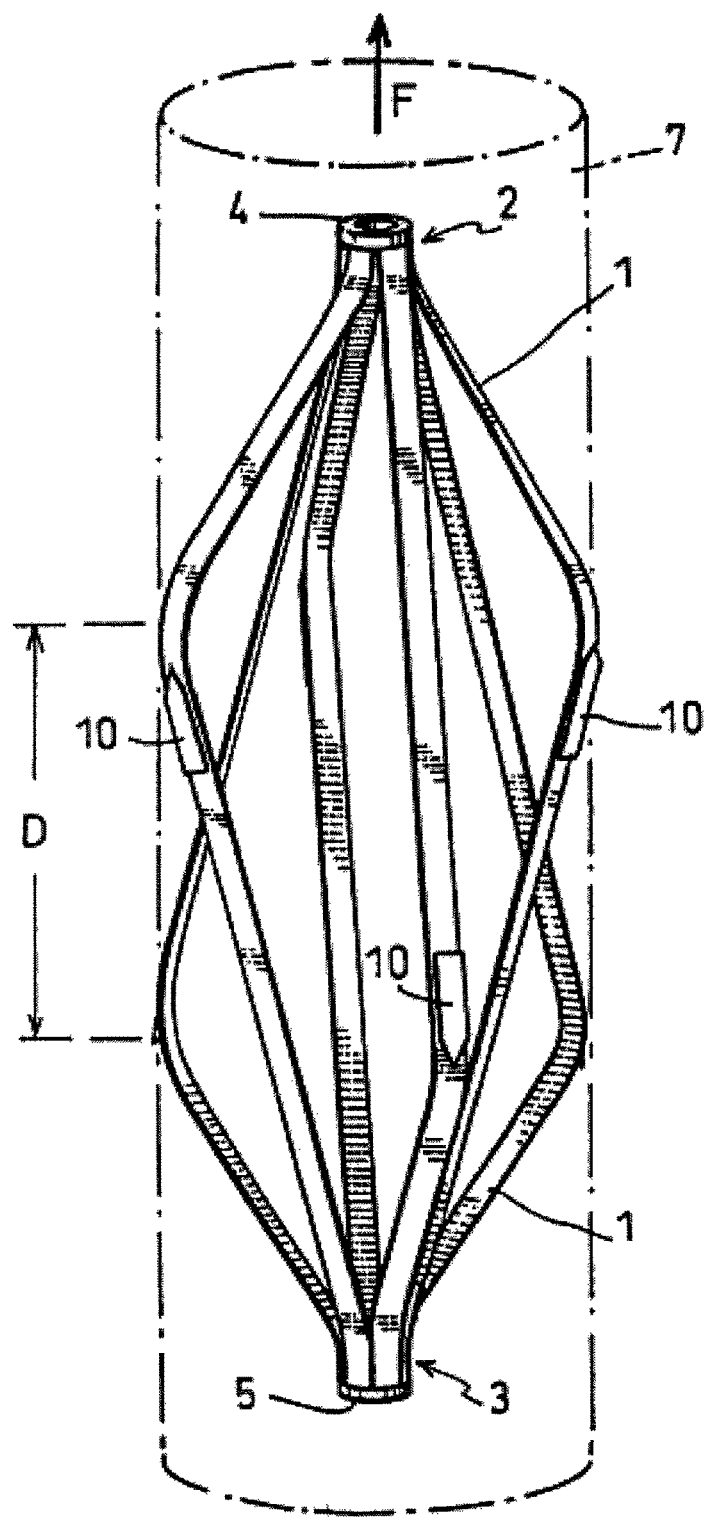
FIG. 32 is a perspective view of a filter device, placed in position in a vein.

Referring now to the drawings, and firstly to FIG. 32, a filter device (hereinafter referred to as "filter") according to the present invention is essentially constituted by an assembly of identical, curved, elastic legs 1, for example six in number, disposed in two's successively in opposite direction, and joined together at their ends 2, 3, particularly by fixing them, for example by electrical spot welding, on two connecting pieces 4, 5.

Each connecting piece is constituted by a substantially cylindrical, hollow piece, the connecting pieces 4 and 5 presenting different internal diameters.

Legs 1, in the out-spread state for use, are angularly distributed in substantially regular manner, for example spaced apart successively in two's by about 60°.

Each leg 1 comprises a convex portion, whose apex 6 is adapted to abut against the inner wall of the vein 7 when the legs are in out-spread state for use.

This convex portion, which may for example be made by burnishing, is closer to one end of leg 1 than the other, with the result that, the legs being identical and mounted successively in two's in opposite direction, said filter abuts on the vein, at the level of apices 6, via two series of points spaced apart longitudinally by a predetermined distance.

The embodiment of the filter described above with regard to FIG. 32 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIG. 32 may be modified according to FIGS. 1-9 above.

Figure 33:
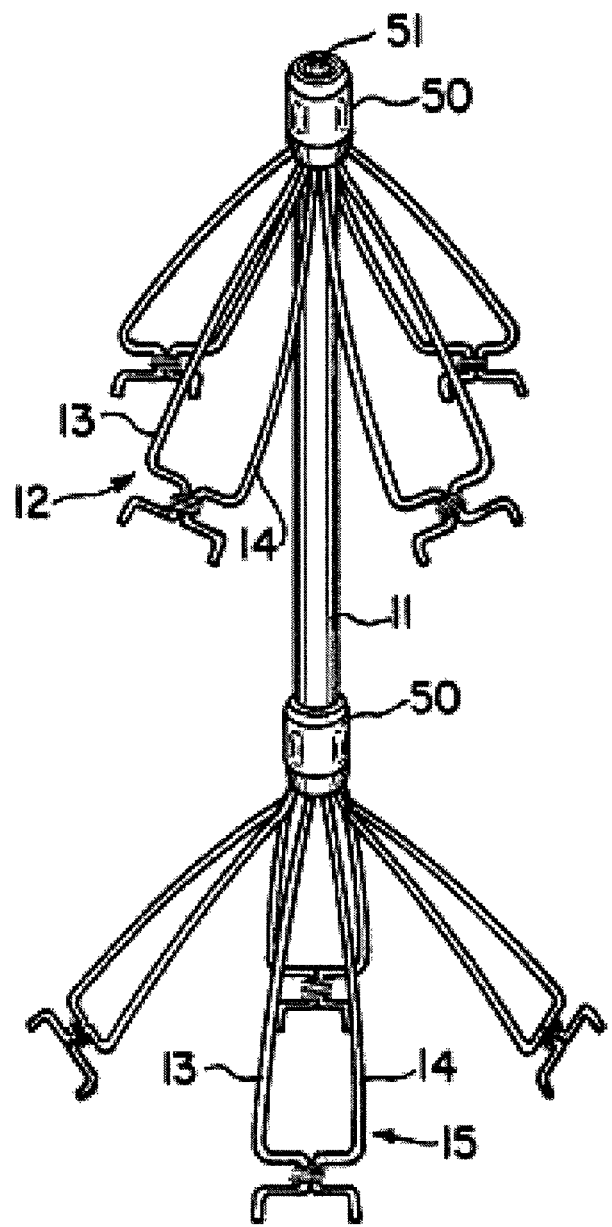
FIG. 33 is an isometric view of an embodiment of an embolus trap.

As shown in FIG. 33, the embolus trap comprises a central cylindrical column 11 to which is attached a plurality of upper elongated loops 12 of filaments 13 and 14, such as metal wire, and a plurality of like lower loops 15. Loops 12 and 15 are assembled in two tiers spaced from one another on column 11. The loops 12 in the upper tier are circumferentially spaced from each other in symmetrical fashion, as are the loops 15 in the lower tier. The loops of adjacent tiers are displaced from each other circumferentially, preferably centrally, so that a loop 12 of the upper tier is centrally located between two loops 15 of the lower tier, and vice versa. The inner ends of adjoining filaments, such as 13 and 14, are anchored in central column 11 and the outer ends of those filaments are joined or abutted to form a closed elongated loop. The outer ends of filaments 13 and 14 are bent toward each other to form short circumferentially extending portions 18 and 19 respectively, and then 180° in the same plane to form oppositely extending circumferential portions 20 and 21 respectively. The extreme ends of portions 20 and 21 are bent radially outwardly into hooks 22. The wires of each loop may be joined at the crowns of the open loops formed by bent portions 18 and 20 of wire 13 and 19 and 21 of wire 14, as by tying the wires over the loops. Those circumferentially bent portions 20 and 21 form a stop or barrier which prevents hooks 22 from penetrating the wall 24 of the passageway 10 sufficient to puncture it.

As shown in FIG. 33, The filaments in each tier are positioned in pairs at the desired spacing around column 11, enclosed in a metal sleeve 50, and are welded thereto at an end of the sleeve. The sleeve 50 with filaments attached is then crimped on column 11. Column 11 is hollow, and preferably rigid, having a central cavity 51 running therethrough.

The embodiment of the filter described above with regard to FIG. 33 may be modified to be a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIG. 33 may be modified according to FIGS. 1-9 above.

In some aspects, any of the above described filters may be modified to include hybrid or dual mode features. One example of a dual mode feature is one that is both radio opaque and also echogenic. In still another aspect, the above described filters may also include a material capture structure as described below, with or without one or more imaging modes as described herein.

In still other alternative embodiments, there is provided a material capture structure having one or more echogenic enhancements alone or in combination with radiopaque enhancements. In one aspect, the filter structure used in a filter includes both echogenic and radio opaque enhancements.

An one aspect, the filter includes material capture structure in the IVC filter will be viewable under fluoroscopic and ultrasound imaging modalities, including appropriate echogenic characteristics to enhance the view of the status or condition of the material capture structure while using IVUS. Enabling the material capture structure to be viewed will allow the physician to appropriately center and verify placement of a filter.

In one aspect, the filter elements or structures are doped to incorporate one or more of echogenic or radio opaque materials or treatments. In one aspect, the filaments or strands or other structures used to form the filter structure or webbing of the filter includes a radiopaque material having high echogenic properties, such as tungsten or gold, but not limited to either.

In other embodiments, one or more filaments or portions of a filament within a material capture structure includes one or more non-metallic echogenic features, such as those described elsewhere in this specification. For example, a filament or portion thereof may include air pockets either added to the material or by the use of materials with entrained air or gas that are used. In one embodiment, an ePTFE suture has echogenic properties due to air content of the ePTFE material. In other aspects, a suture material or a filament or polymer strand may also include dimpled/roughened/matrix/sponge materials, additives, or modifications to provide or enhance the overall echogenic nature of the suture, filament, material or material capture structure, in whole or in part.

In one aspect, these additional materials may assist the physician in centering or placing a filter within a vessel. In another aspect, this improvement is used in conjunction with IVUS will enable the adequate viewing of the filter portion of the filter and will allow for co-registration of filter placement along with an accurate entry/removal of the catheter through the webbing of the filter.

The advantages of this inventive aspect of a filter include, for example and not limitation, filter placement, accurate representation of filter location, ease of introducing/retracting catheter, more viewable space for more accurate assessments, ability to co-register filter location with IVUS and/or ability to better place filter in desired location.

Still other aspects of the use of the innovative filter include, for example, deployment of filters, positioning of filters, sizing of filters, and estimated treatment lengths as well as suture and/or material capture structure visibility. In still other aspects of the use of the innovative filter include, for example, deployment of a vena cava filter, positioning of an IVC filter, sizing of an IVC filter, and estimated treatment lengths as well as enhanced suture visibility.

In one embodiment, there is an IVC filter delivery system with an enclosed IVC filter. This filter would have a mesh, suture, web or other material capture structure suited to the anticipated filter use. The mesh, suture, web or other material capture structure has one or more components that is doped with a highly radiopaque material for better visibility under flouro and good echogenicity for better viewing under IVUS guidance. In still further alternative embodiments, the techniques described above may be applied to one or more material capture structure described in U.S. Patent Application Publication No. US 2008/0147111 entitled "Endoluminal Filter with Fixation" filed Jun. 4, 2008 as U.S. patent application Ser. No. 11/969,827, (the "'7111 publication") incorporated herein by reference in its entirety for all purposes. More particularly, the aspects of modifying a material capture structure to exhibit radio opaque, echogenic of combinations of radio opaque and echogenic characteristics may be applied to the various embodiments illustrated and described in FIGS. 30-34B, 38A-38B, 39-67, and 83-87. In one particular aspect, the filament/strand/suture 461 shown in FIG. 58 of the '7111 publication may be coated or doped as described above alone or in combination with the illustrated pharmacological coating 466.

In still another alternative aspect, any of the material capture structures in the '7111 publication may be combined with any of the filters illustrated and described in FIGS. 9-33. The material capture structures may be joined to the wires or other supports in the filters described herein to provide additional kinds of filtering capabilities in addition to or in place of the filtering capabilities of the filter so described.

In some embodiments, a pressure sensor and/or an intravascular ultrasound (IVUS) transducer can be added to or incorporated into a delivery system and method for use with any of the filters described herein. The pressure sensor can be used to measure the pressure at various positions within the vasculature, which can be used to determine blood flow, while the intravascular ultrasound (IVUS) transducer can be used to measure fluid flow and/or provide imaging within the vessel. These activities can be performed in cooperation with any of the filter embodiments described herein. In some embodiments, the pressure sensor and/or IVUS transducer can be incorporated into the guidewire at one or more locations, such as the distal end or distal portion of a guidewire, as described in U.S. Pat. Nos. 8,277,386, 6,106,476 and 6,780,157 which are hereby incorporated by reference in their entireties for all purposes, as well as being incorporated into intermediate and proximal portions of the guidewire. The guidewire with the pressure sensor and/or the IVUS transducer can be used much like a normal guidewire to help navigate the delivery device through the vasculature, with the added benefit of providing pressure measurements and ultrasound imaging to help in the navigation, to visualize the device placement site, and to monitor and ensure proper device deployment. In some embodiments, the IVUS transducer generates image slices as it is advanced and retracted which can then be assembled together to form a three dimensional reconstruction of the vasculature and/or the device within the vasculature. In some embodiments, the guidewire with the pressure sensor and/or IVUS transducer can be fastened to a catheter in a similar manner to that described below for a catheter having a pressure sensor and/or IVUS transducer that is fastened to another catheter.

Figure 34A:
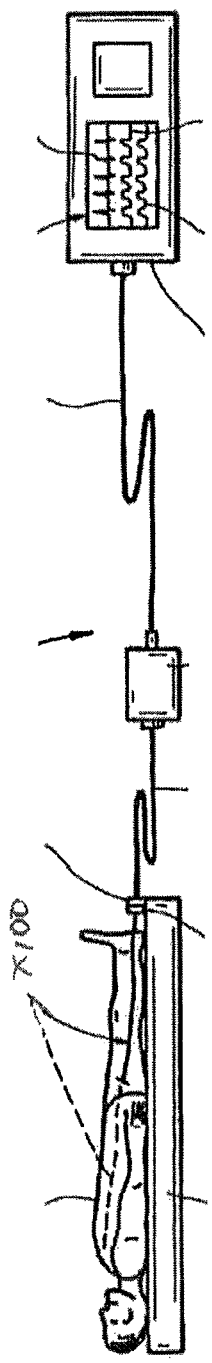
FIGS. 34A-34C illustrate an example of a guidewire having both a pressure sensor and an IVUS transducer located at the distal portion of the guidewire.
Figure 34B:
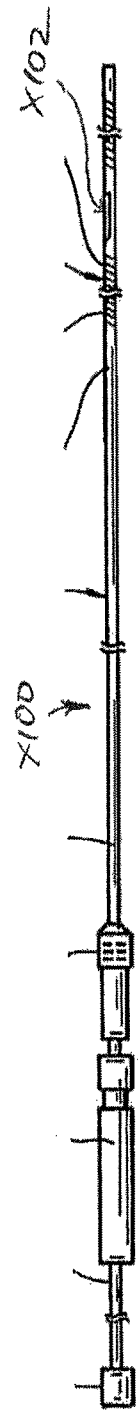
Figure 34C:
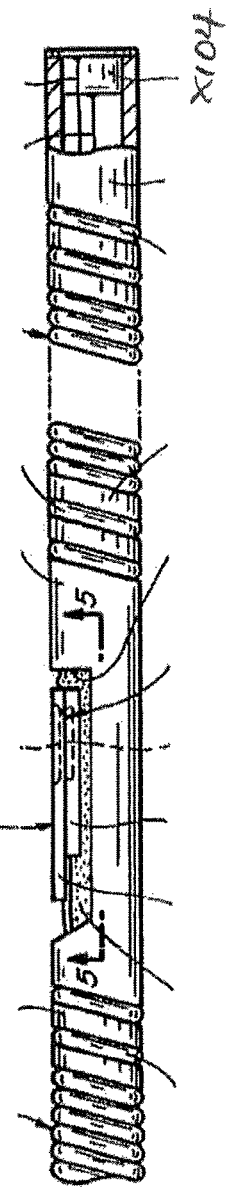

FIGS. 34A-34C illustrate an example of a guidewire X100 having both a pressure sensor X102 and an IVUS transducer X104 located at the distal portion of the guidewire X100. In some embodiments, the pressure sensor X102 can be made from a semiconductor material, such as silicon, that is formed into a diaphragm and can be located proximally of the distal tip, while the IVUS transducer X104 can be located at the distal tip of the guidewire X104.

In some embodiments, the pressure sensor and/or IVUS transducer can be located on a catheter in a similar configuration to the guidewire. For example, the IVUS transducer can be located on the distal tip of the catheter while the pressure sensor(s) can be located proximally of the IVUS transducer at one or more locations along the catheter body, from the distal portion of the catheter to an intermediate portion of the catheter to the proximal portion of the catheter. The pressure and/or imaging catheter can be used in parallel with the delivery or retrieval device or any other catheter that is inserted into the vasculature. In some embodiments, the pressure and/or imaging catheter can be fastened to the delivery or retrieval device or other catheter by, for example, enclosing both catheters in a sheath or larger catheter or by fusing the two catheters together. For example, U.S. Pat. Nos. 6,645,152 and 6,440,077, both to Jung et al. and hereby incorporated by reference in their entireties for all purposes, discloses an intravascular ultrasound catheter joined together in parallel with a vena cava filter delivery device to guide placement of the filter in the vena cava. The pressure and/or imaging catheter can be used for the same purposes as the pressure and/or imaging guidewire.

Figures 35A, 35B, 35C, 35D:
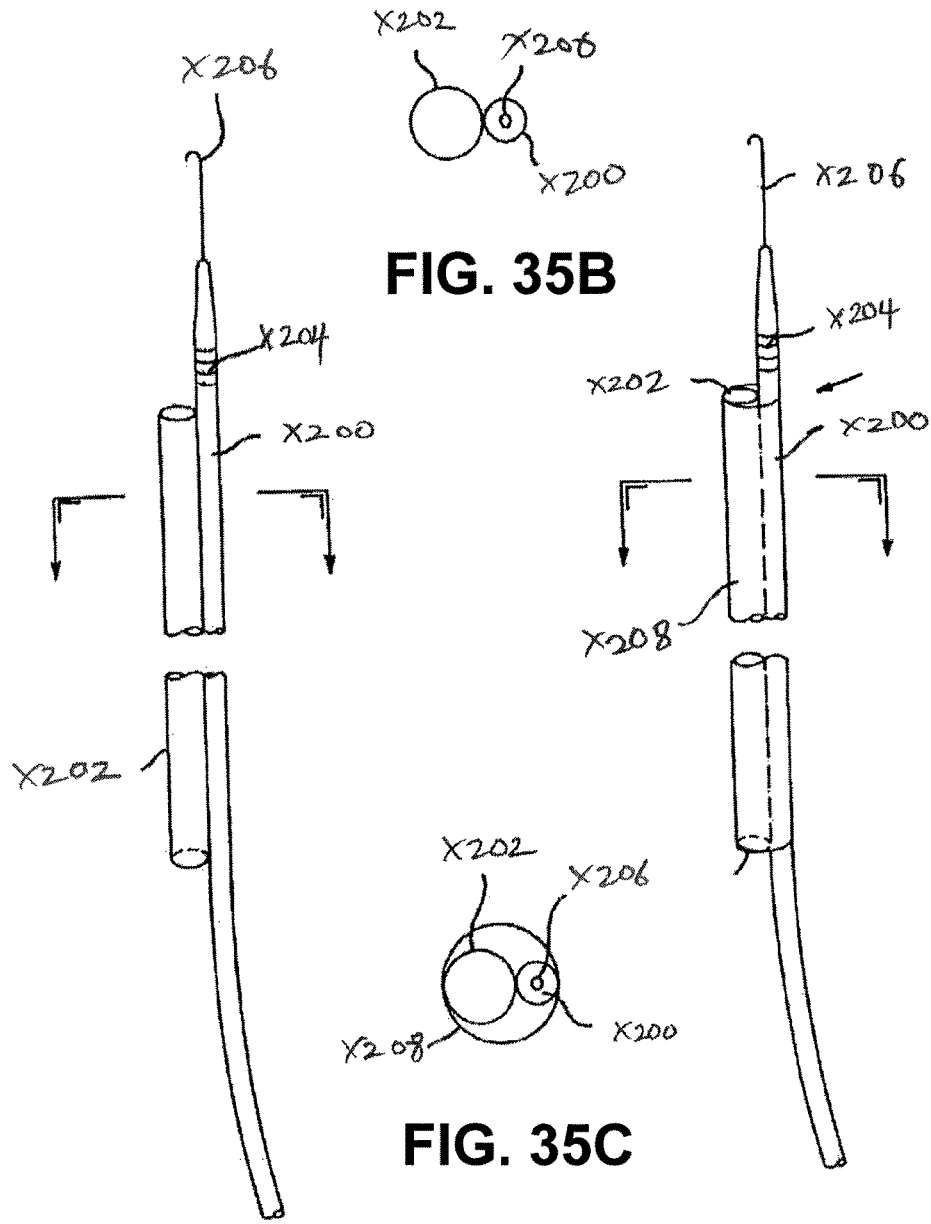
FIGS. 35A-35D illustrate two embodiments of an intravascular ultrasound catheter joined together in parallel with a catheter.

FIGS. 35A-35D illustrate two embodiments of an intravascular ultrasound catheter X200 joined together in parallel with a catheter X202 that can be used, for example, to deliver a device to a location with the vasculature, such as a vena cava filter to the vena cava. The intravascular ultrasound catheter X200 can have an IVUS transducer X204 located on the distal portion of the IVUS catheter X200. The IVUS transducer X204 can be a solid state transducer that is disk shaped or cylindrically shaped with a hole to allow passage of a guidewire X206 or other device through the IVUS catheter X200. As shown in FIGS. 35A and 35B, the IVUS catheter X200 and the delivery catheter X202 can be joined together in parallel without a sheath by adhering or fusing the two catheters together. FIGS. 35C and 35D illustrate the same IVUS catheter X200 and delivery catheter X202 fastened together using a sheath X208.

In some embodiments as illustrated in FIGS. 36A and 36B, the pressure sensor and/or IVUS transducer can be integrated into the delivery or retrieval catheter X300 or device itself. In one aspect, the device is any of the filters having enhanced capabilities described herein. For example, the IVUS transducer X302 can be integrated into the distal tip or end of the catheter X300 or device. The pressure sensor X304 can be located on a distal portion of the catheter shaft proximally of the IVUS transducer X302. A wire can extend from the IVUS transducer X302 and/or pressure sensor X304 to one or more connectors X306 located at the proximal end of the catheter X300. The connector(s) X306 can be used to connect the IVUS transducer X302 and/or pressure sensor X304 to an imaging system and/or processing system. In the illustrated embodiment, the catheter X300 can be used to deliver a vena cava filter X308 to the vena cava. The catheter X300 can additionally have a telescoping sleeve or pusher rod to deploy the vena cava filter X308, or alternatively, the outer catheter sheath can be retracted to deployed the filter. The IVUS transducer can provide positioning guidance and determine the relative location of the filter by advancing and retracting the IVUS transducer X302 on the catheter X300 to generate a plurality of image slices that can be assembled to reconstruct a three dimensional image.

Use of the ultrasound imaging system allows the operator to deliver the device without fluoroscopy or using less fluoroscopy, thereby reducing the radiation exposure to the patient, while allowing more accurate evaluation of the vasculature, aiding placement of the device and allowing confirmation that device placement was proper. The imaging can be used to aid in the deployment of the filters or other devices. The vasculature and implant location can be imaged prior to deployment, after deployment and/or during deployment. The imaging can be used to aid in positioning of the filter or device within the vasculature. The imaging can be used to image the deployment location and determine the appropriate sizing of the filter or other device. The imaging can be used to help estimate treatment duration.

Although an imaging systems described above have been ultrasound based, other imaging systems can be used instead or in addition. For example, the imaging system can be based on intravascular ultrasound (IVUS), Forward-Looking IVUS (FLIVUS), optical coherence tomography (OCT), piezoelectric micro-machined ultrasound traducer (PMUT), and FACT.

Additional aspects of the formation and use of echogenic materials is made with reference to the following US Patents and Patent Publications, each of which is incorporated herein by reference in its entirety: US 2010/0130963; U.S. Pat. Nos. 5,921,933; 4,276,885; 4,572,203; 4,718,433; 4,442,843; 5,327,891; 4,401,124; 4,265,251; 4,466,442; 4,718,433; 5,081,997; 5,289,831; and 5,201,314. Additional details of various filter designs described herein may be obtained with reference to the following U.S. Pat. Nos. 3,952,747; 4.817,600; 5,059,205; 5,242,462; 6,620,183; 6,217,600; 8,273,099; 4,494,531; 4,425,908; 4,832,055; 5,133,733; 3,540,431; 5,344,427; 5,725,550; 4,619,246; 4,990,156; 5,234,458; and 4,643,184, each of which is incorporated herein by reference in its entirety.

What is claimed is:

1. A filter comprising:
    a hub; and
    a plurality of legs or wires or segments extending from the
        hub; wherein the plurality of legs or wires or segments comprise a first section having a first pattern of voids formed therein to provide an enhanced echogenic characteristic of the first section and a second section having a second pattern of voids formed therein to provide an enhanced echogenic characteristic of the second section, wherein the first pattern of voids is different than the second pattern of voids.

2. The filter of claim 1 wherein the first pattern of voids is filled with air.

3. The filter of claim 2 wherein the second pattern of voids is filled with air.

4. The filter of claim 2 wherein the second pattern of voids is filled with an echogenic material.

5. The filter of claim 1 wherein the first pattern of voids is filled with an echogenic material.

6. The filter of claim 1 wherein the first pattern of voids are air bubbles formed within the first section.

7. The filter of claim 1 wherein the first pattern of voids are air bubbles formed within an ePTFE material forming the first section of the portion of one or more of the legs or wires or segments.

8. The filter of claim 1 wherein the first pattern of voids is scaled to a suitable size, shape and orientation for use with an intravascular ultrasound system.

9. The filter of claim 1 further comprising at least one fixation element and wherein the fixation element comprises a third pattern of voids to provide an enhanced echogenic characteristic of the at least one fixation element or the filter.

10. A filter comprising:
a hub; and
a plurality of segments extending from the hub, wherein a first of the plurality of segments comprises a first pattern of voids formed therein to provide an enhanced echogenic characteristic of the first of the plurality of segments, wherein a second of the plurality of segments comprises a second pattern of voids formed therein to provide an enhanced echogenic characteristic of the second of the plurality of segments, wherein the first pattern is different than the second pattern.

11. The filter of claim 10 wherein the first pattern of voids comprise an air gap formed in the first segment.

12. The filter of claim 11 wherein the second pattern of voids comprises an air gap formed in the second segment.

13. The filter of claim 11 wherein the second pattern of voids is filled with an echogenic material.

14. The filter of claim 10 wherein the first pattern of voids comprise a gap formed in the first segment, wherein the gap is filled with an echogenic material.

15. The filter of claim 10 wherein the first pattern of voids comprises an air pocket in an ePTFE material.

* * * * *